(12) United States Patent
Burkholz et al.

(10) Patent No.: US 11,291,803 B2
(45) Date of Patent: Apr. 5, 2022

(54) CATHETER SYSTEM WITH GUIDEWIRE ADVANCEMENT ELEMENT

(71) Applicant: Becton, Dickinson and Company, Franklin Lakes, NJ (US)

(72) Inventors: Jonathan Karl Burkholz, Salt Lake City, UT (US); Joseph Spataro, Cottonwood Heights, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 174 days.

(21) Appl. No.: 16/239,101

(22) Filed: Jan. 3, 2019

(65) Prior Publication Data

US 2019/0209812 A1    Jul. 11, 2019

Related U.S. Application Data

(60) Provisional application No. 62/616,053, filed on Jan. 11, 2018.

(51) Int. Cl.
*A61M 25/06*    (2006.01)
*A61M 25/09*    (2006.01)

(52) U.S. Cl.
CPC .. *A61M 25/0606* (2013.01); *A61M 25/09041* (2013.01); *A61M 25/0631* (2013.01); *A61M 25/0637* (2013.01)

(58) Field of Classification Search
CPC .......... A61M 25/0606; A61M 25/0637; A61M 25/09041
See application file for complete search history.

(56) References Cited

U.S. PATENT DOCUMENTS

| 5,279,590 A | * | 1/1994 | Sinko | A61M 25/0631 |
| | | | | 604/110 |
| 2012/0197200 A1 | | 8/2012 | Belson | |
| 2016/0045715 A1 | * | 2/2016 | Galgano | A61M 25/09 |
| | | | | 604/510 |
| 2018/0296799 A1 | * | 10/2018 | Horst | A61M 25/09041 |
| 2020/0001051 A1 | * | 1/2020 | Huang | A61M 25/0693 |

FOREIGN PATENT DOCUMENTS

| WO | 2010/111285 | 9/2010 |
| WO | 2016/007442 | 1/2016 |
| WO | 2017/074677 | 5/2017 |

* cited by examiner

*Primary Examiner* — Emily L Schmidt
(74) *Attorney, Agent, or Firm* — Kirton McConkie; Whitney Blair; Kevin Stinger

(57) ABSTRACT

An intravenous catheter system may include a catheter adapter, which may be integrated. The intravenous catheter system may also include a housing coupled to a proximal end of the catheter adapter, an introducer needle having a proximal end, a distal tip, and a needle lumen extending between the proximal end of the introducer needle and the distal tip, a guidewire disposed within the housing and the needle lumen, and a guidewire advancement element. The housing may include a proximal end, a distal end, and a slot. A proximal end of the introducer needle may be secured within the housing. The guidewire advancement element may extend through the slot and be moveable along the slot in a distal direction to move the guidewire from a retracted position to an advanced position, in which the guidewire may extend beyond the distal tip.

8 Claims, 20 Drawing Sheets

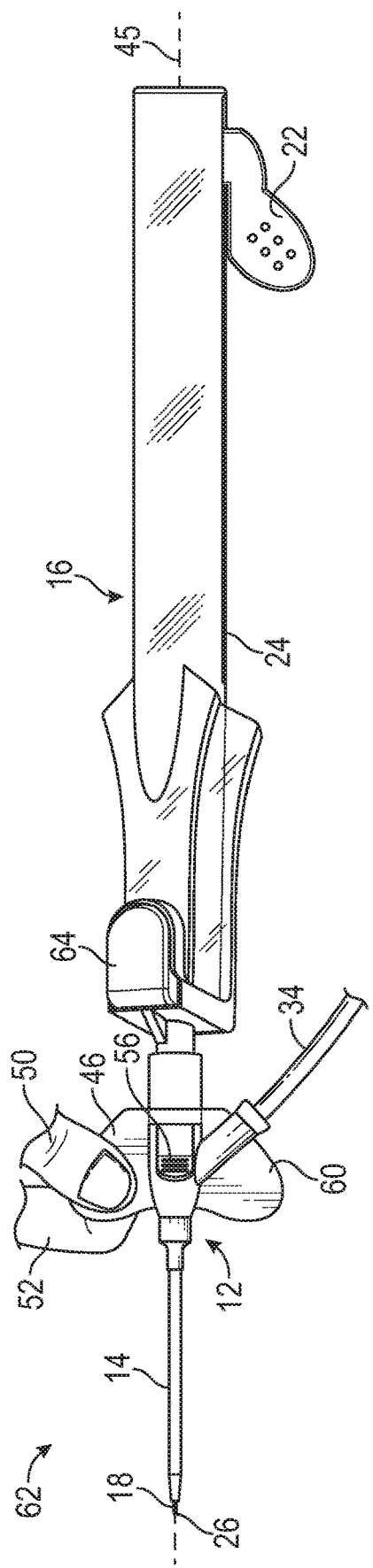
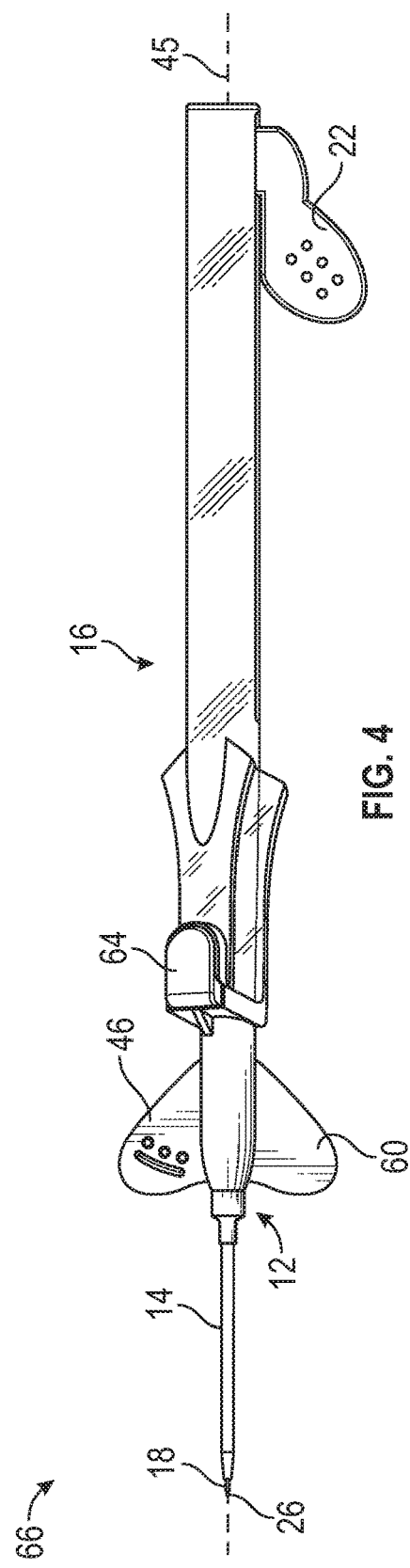
FIG. 3D
FIG. 4

CATHETER SYSTEM WITH GUIDEWIRE ADVANCEMENT ELEMENT

RELATED APPLICATIONS

This application claims the benefit of U.S. Provisional Patent Application No. 62/616,053, filed on Jan. 11, 2018, entitled "CATHETER SYSTEM WITH GUIDEWIRE ADVANCEMENT ELEMENT," which is incorporated herein in its entirety.

BACKGROUND OF THE INVENTION

Intravenous (IV) catheters are commonly used for a variety of infusion therapies. For example, IV catheters may be used for infusing normal saline solution, various medicaments, or total parenteral nutrition into a patient. IV catheters may also be used for withdrawing blood from the patient.

A common type of IV catheter is an over-the-needle peripheral IV catheter. As its name implies, the over-the-needle peripheral IV catheter may be mounted over an introducer needle having a sharp distal tip. The sharp distal tip may be used to pierce skin and a vein of the patient. Insertion of the over-the-needle peripheral IV catheter into the vein may follow the piercing of the vein by the introducer needle. The introducer needle and the over-the-needle peripheral IV catheter are generally inserted at a shallow angle through the skin into the vein of the patient with a bevel of the introducer needle facing away from the skin of the patient.

In order to verify proper placement of the introducer needle and/or the over-the-needle peripheral IV catheter in the vein, a clinician generally confirms that there is "flashback" of blood in a flashback chamber of a catheter assembly. Once placement of the introducer needle has been confirmed, the clinician may temporarily occlude flow in the vein and withdraw the introducer needle, leaving the catheter in place for future blood withdrawal or fluid infusion.

Patients with difficult and/or fragile vein access present significant challenges to the clinician responsible for inserting and securing in the vein an IV device, such as the over-the-needle peripheral IV catheter. In some instances, a guidewire may be used to facilitate placement of a catheter tip within the vein of the patient, which may result in less vein-related trauma. Upon successful placement of the catheter tip within the vein, the guidewire may be withdrawn in conjunction with the introducer needle.

BRIEF SUMMARY OF THE INVENTION

The present disclosure relates generally to an intravenous (IV) catheter system and related devices and methods. As used in the present disclosure, the term "distal" refers to a portion of the IV catheter system, or component thereof, that is farther from a user, and the term "proximal" refers to a portion of the IV catheter system, or component thereof, that is closer to the user. As used in the present disclosure, the term "user" may refer to a clinician, doctor, nurse, or any other care provider and may include support personnel.

In some embodiments, the IV catheter system may include a guidewire to facilitate catheter placement in a patient, who may have difficult and/or fragile venous access. In some embodiments, the IV catheter system may also be integrated and/or accommodate various clinical insertion techniques. For example, the IV catheter system may accommodate one or more of the following clinical insertion techniques: a winged grip, a nested winged grip, a ported grip, and a central grip.

In some embodiments, the IV catheter system may include one or more of the following: a catheter adapter, a catheter, a housing, a grip, an introducer needle, the guidewire, and a guidewire advancement element. In some embodiments, the housing may be proximate and/or coupled to a proximal end of the catheter adapter. In some embodiments, the housing may include a proximal end, a distal end, and a slot.

In some embodiments, the guidewire advancement element may extend through the slot and may be moveable along the slot in a distal direction to move the guidewire from a retracted position to an advanced position. In some embodiments, the guidewire may extend beyond a distal tip of the introducer needle when the guidewire is in the advanced position.

In some embodiments, the introducer needle may include a proximal end, a distal tip, and a needle lumen extending between the proximal end of the introducer needle and the distal tip. In some embodiments, the proximal end of the introducer needle may be secured within the housing. For example, the proximal end of the introducer needle may be coupled to a needle hub, which may be disposed within the housing. In some embodiments, the guidewire may be disposed within the needle lumen. In some embodiments, the guidewire may move within the needle lumen when the guidewire is moved from the retracted position to the advanced position.

In some embodiments, the IV catheter system may include an integrated catheter adapter. In further detail, in some embodiments, the IV catheter system may include a catheter adapter having an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System.

In these and other embodiments, the catheter adapter may include a first port and a second port. In some embodiments, a lumen of the catheter adapter may include a first lumen, a second lumen, and a common lumen. In some embodiments, the first port may form the first lumen and/or the second port may form the second lumen. In some embodiments, the first and second lumens may join at the common lumen. In some embodiments, the first lumen may be generally aligned with the common lumen and/or the second port may correspond to a side port.

In some embodiments, the catheter adapter may include a septum, which may be a low-drag septum. In an integrated catheter adapter, the septum may be disposed within the first lumen, which may correspond to a "needle channel." In some embodiments, the septum may close off the first lumen from an external environment surrounding the catheter adapter. Thus, the septum may at least substantially seal the first port and prevent fluid from exiting the catheter adapter through the first port. In some embodiments, a fluid pathway of the catheter assembly during fluid infusion and/or blood withdrawal may extend through the second port and not the first port. In some embodiments, a majority or substantially all of the fluid and/or the blood may flow through the second port and not the first port.

In some embodiments, the second port may be coupled to an extension tube. In some embodiments, the second lumen of the catheter adapter may be connectable to blood withdrawal or infusion means via the extension tube that may extend from the second port of the catheter adapter.

In some embodiments, the slot may be disposed in any portion of the housing. In some embodiments, the slot may be disposed in a left or right side of the housing. In some embodiments, the slot may be disposed in a top or bottom of the housing. In some embodiments, the slot may be aligned with a central plane of the IV catheter system. In some embodiments, the catheter adapter may include a wing extending outwardly from a right side of a body of the catheter adapter. In these and other embodiments, guidewire advancement element may be disposed on a left side of the IV catheter system and/or aligned with the central plane of the IV catheter system, which may facilitate access to the guidewire advancement element by the user when the user also grips the wing. As used in the present disclosure, the terms "left" and "right" refer to a portion of the IV catheter system, or component thereof, that are on the left and right sides, respectively, from the perspective of the user facing a distal end of the IV catheter system from a proximal end of the housing when the IV catheter system is inserted into the vein of the patient.

In some embodiments, the IV catheter system may include the grip, which may extend outwardly from a body of the housing. In some embodiments, the grip may extend through the slot or another slot in the housing. In some embodiments, the grip may be disposed in various locations with respect to the IV catheter system, which may facilitate access to the grip by the user. In some embodiments, the grip may include a shape that generally corresponds to the shape of the wing. In some embodiments, the grip may be positioned directly beneath wing so that the wing and the grip may be sandwiched between a thumb and index finger of a first hand of the user during insertion of the catheter into the vasculature of the patient. In these embodiments, the user may easily withdraw the housing from the catheter adapter by simply sliding the index finger proximally with respect to the thumb thereby causing the grip to slide proximally away from the wing. In some embodiments, a ridge on an upper surface of the grip may prevent proximal movement of the catheter adapter with respect to the housing. In some embodiments, the grip may be configured to be positioned above or adjacent to the wing.

In some embodiments, in response to movement of the guidewire advancement element along the slot in the distal direction to move the guidewire from the retracted position to the advanced position, the guidewire advancement element may couple to the grip. In some embodiments, in response to movement of the guidewire advancement element along the slot in the distal direction to move the guidewire from the retracted position to the advanced position, the guidewire advancement element may not couple to the grip. In some embodiments, the introducer needle may be coupled to the grip. In particular, in some embodiments, the introducer needle may be coupled to a portion of the grip disposed within the housing, which may include the needle hub.

In some embodiments, the guidewire advancement element and/or the grip may be moveable along the slot in the distal and/or proximal direction. In some embodiments in which the guidewire advancement element becomes coupled to the grip, in response to movement of the guidewire advancement element and/or the grip along the slot in the proximal direction, the guidewire and the introducer needle may move proximally within the housing. In some embodiments, in response to movement of the guidewire advancement element and/or the grip along the slot in the proximal direction, the introducer needle may be shielded within the housing such that the distal tip of the introducer needle is contained within the housing. Additionally or alternatively, in some embodiments, in response to movement of the guidewire advancement element and/or the grip along the slot in the proximal direction, the guidewire may be shielded within the housing such that a distal end of the guidewire is contained within the housing.

In some embodiments, the housing may include the other slot, which may be disposed in any portion of the housing. In some embodiments, the other slot may be disposed in a top or bottom of the housing. In some embodiments, the other slot may be disposed in a left or right side of the housing. In some embodiments, the other slot may be aligned with a central plane of the IV catheter system.

In some embodiments, the grip may be moveable along the slot or the other slot in the distal and/or proximal direction. In some embodiments, in response to movement of the grip along the other slot in the proximal direction, the guidewire, the guidewire advancement element, and the introducer needle may move proximally within the housing.

In some embodiments, the grip may not be coupled to the guidewire advancement element, however, in response to movement of the grip along the slot or the other slot in the proximal direction, the grip may move the guidewire advancement element proximally. For example, in response to movement of the grip along the slot or the other slot in the proximal direction, the grip may contact a distal end of the guidewire advancement element and drive movement the guidewire advancement element proximally.

In some embodiments, in response to movement of the grip along the other slot in the proximal direction, the introducer needle may be shielded within the housing such that the distal tip of the introducer needle is contained within the housing and/or a portion of the grip may be shielded within the housing. Additionally or alternatively, in some embodiments, in response to movement of the grip along the other slot in the proximal direction, the guidewire may be shielded within the housing such that a distal end of the guidewire is contained within the housing.

In some embodiments, in response to shielding of the distal tip of the introducer needle within the housing and/or shielding of the distal end of the guidewire within the housing, the housing may be configured to separate and/or uncouple from the catheter adapter. In further detail, in some embodiments, in response to shielding of the distal tip of the introducer needle and/or shielding of the distal end of the guidewire within the housing, a coupling mechanism between the catheter adapter and the housing may be released, automatically and/or by the user. For example, the coupling mechanism may include a latch mechanism or any other suitable type of coupling mechanism. In some embodiments, the user may twist or rotate an outer sleeve of the housing with respect to an inner sleeve of the housing and the catheter adapter, which may uncouple the catheter adapter from the housing, as will be explained in further detail.

In some embodiments, the catheter adapter and/or the housing may include a thumb tab. In some embodiments, the thumb tab may be laterally offset from a portion of the grip that may be gripped by the user, such as, for example, a winged portion of the grip, which may facilitate access to the guidewire advancement element by the user when the user grips the IV catheter system in a ported grip, for example. In some embodiments, the thumb tab may be aligned with a central plane of the IV catheter system and/or disposed on a top of the catheter adapter and/or the housing.

In some embodiments, a method of IV catheter insertion into vasculature of a patient may include gripping, with a first hand of a user, the wing of the catheter adapter and/or the grip of the housing. In some embodiments, the method may include gripping, with a second hand of the user, the guidewire advancement element. In some embodiments, the method may include inserting the introducer needle and the catheter into the vein when one or more of the following are being gripped: the wing of the catheter adapter, the grip of the housing, and the guidewire advancement element. In some embodiments, after the introducer needle and the catheter are inserted into the vein, the method may include moving the guidewire advancement element in the distal direction to move the guidewire to the advanced position with the second hand. In some embodiments, the first hand may correspond to the right hand of the user, and the second hand may correspond to the left hand of the user.

In some embodiments, after the guidewire advancement element is moved in the distal direction to the advanced position, the catheter may be further advanced into the vein by moving the catheter adapter distally while holding the grip stationary.

In some embodiments, the gripping of the wing with the first hand of the user and the gripping of the guidewire advancement element with the second hand of the user may occur at a same time or simultaneously. In some embodiments, the guide wide advancement element may be advanced when the guide wide advancement element is gripped. In some embodiments, the wing of the catheter adapter may be laterally offset from the guidewire advancement element to facilitate use of both hands of the user with respect to the IV catheter system. For example, the wing and the slot may be disposed on opposite sides of the IV catheter system.

In some embodiments, the IV catheter system may be configured to be gripped by the user according to a number grips that may facilitate insertion of the introducer needle into the vasculature of the patient and/or advancement of the catheter along the guidewire. For example, gripping the wing of the catheter adapter may include sandwiching the wing and the grip between a thumb and index finger of the first hand of the user. In some embodiments, the wing and the grip may be sandwiched between the thumb and the index finger of the first hand of the user at a same time as the guidewire advancement element is advanced distally and/or moved proximally with the second hand.

In some embodiments, the wing may be a first wing, and the catheter adapter may include a second wing opposite the first wing. Thus, in some embodiments, the catheter adapter may include multiple wings, such as, for example, the wing extending outwardly from the right side of the body of the catheter adapter and another wing extending outwardly from the left side of the body of the catheter adapter.

In some embodiments, gripping the first wing may include placing a middle finger of the first hand on an upper surface of the first wing. In some embodiments, at a same time as the first wing of the catheter adapter is gripped with the first hand and the guidewire advancement element is gripped with the second hand, the user may grip the second wing and the thumb tab by placing an index finger of the first hand on an upper surface of the second wing and a thumb of the first hand on the thumb tab.

In some embodiments, the method may include moving the guidewire advancement element and/or the grip along the slot in the proximal direction. In some embodiments, in response to moving the guidewire advancement element and/or the grip along the slot in the proximal direction, the guidewire, the grip, and the introducer needle may move towards the proximal end of the housing. In some embodiments, the method may include moving the grip along another slot in the proximal direction, and the guidewire, the guidewire advancement element, and the introducer needle may move towards the proximal end of the housing in response to moving the grip along the other slot.

It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which:

FIG. 3D is a top view of another example IV catheter system, illustrating the user gripping the IV catheter system according to an example winged grip, according to some embodiments;

FIG. 4 is a top view of another example IV catheter system, according to some embodiments;

DETAILED DESCRIPTION OF THE INVENTION

Figure 1A:
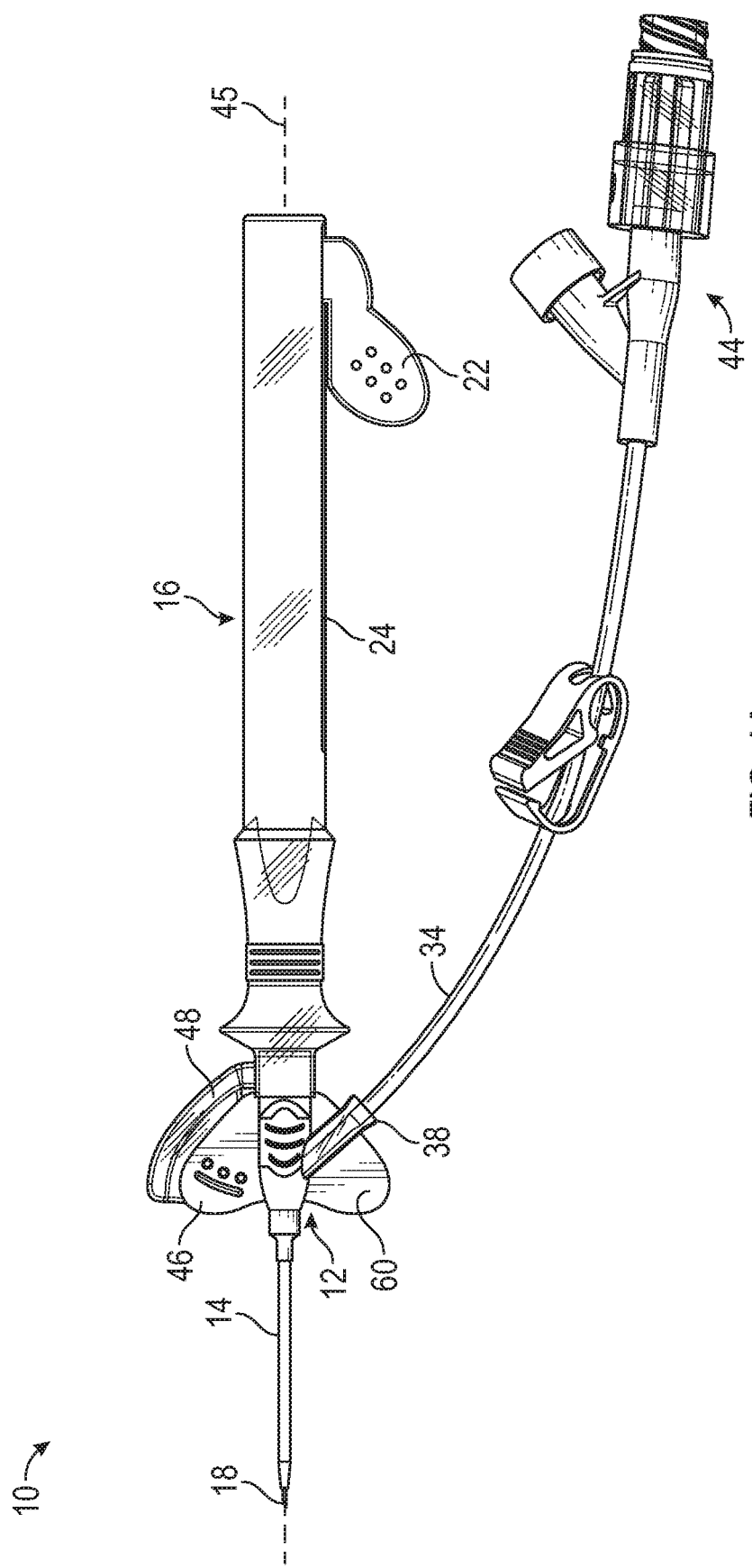
FIG. 1A is a top view of an example IV catheter system, illustrating an example guidewire in the retracted position, according to some embodiments.

The present disclosure relates generally to an intravenous (IV) catheter system and related devices and methods. In some embodiments, the IV catheter system may include a guidewire to facilitate catheter placement in a patient, who may have difficult and/or fragile venous access. In some embodiments, the IV catheter system may also be integrated and/or accommodate various clinical insertion techniques. For example, the IV catheter system may accommodate one or more of the following clinical insertion techniques: a winged grip, a nested winged grip, a ported grip, and a central grip.

Referring now to FIGS. 1A-2B, in some embodiments, the IV catheter system 10 may include one or more of the following: a catheter adapter 12, a catheter 14, a housing 16, an introducer needle 18, the guidewire 20, and a guidewire advancement element 22. In some embodiments, the housing 16 may be proximate and/or coupled to a proximal end of the catheter adapter 12. In some embodiments, the housing 16 may include a proximal end, a distal end, and a slot 24.

Figure 1B:
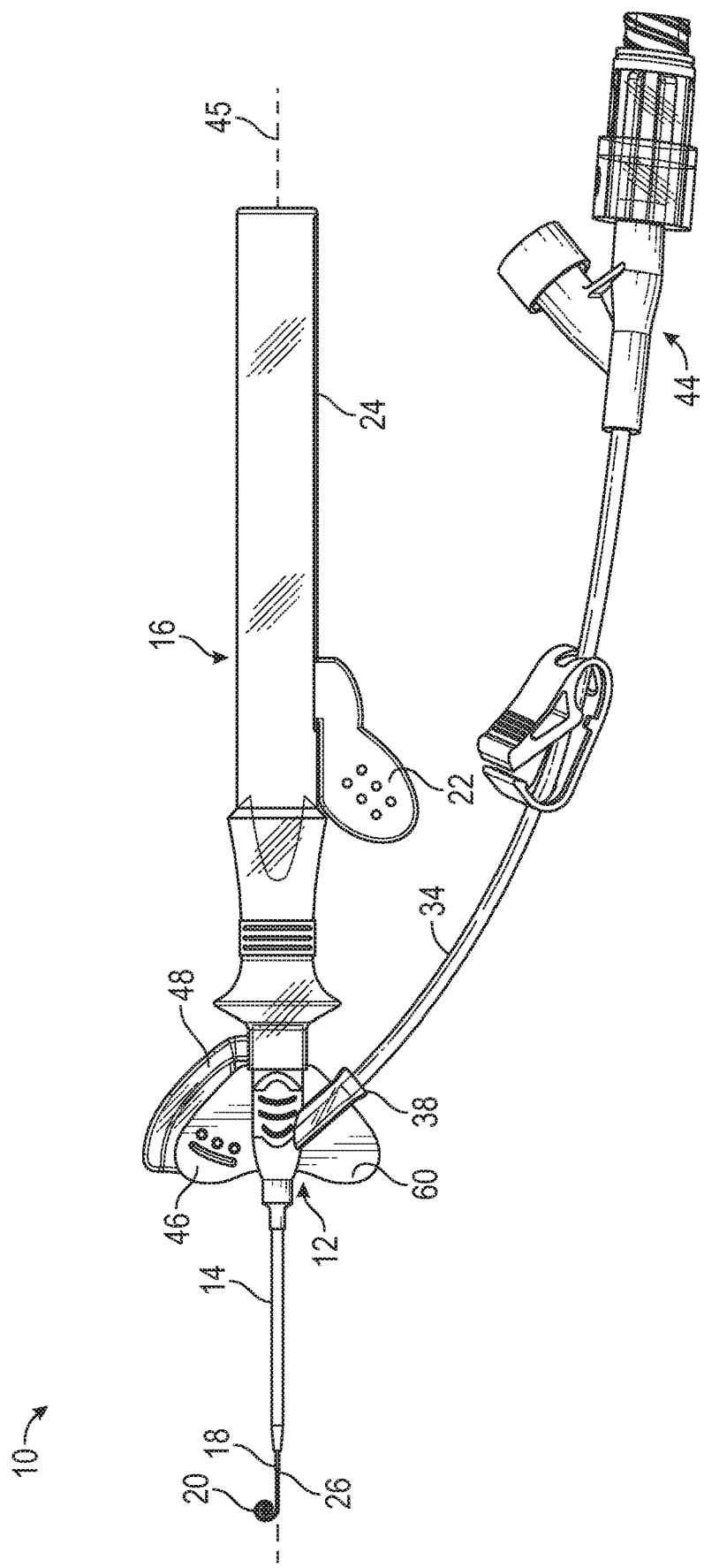
FIG. 1B is a top view of the IV catheter system of FIG. 1A, illustrating the guidewire in the advanced position, according to some embodiments.

In some embodiments, the guidewire advancement element 22 may extend through the slot 24 and may be moveable along the slot 24 in a distal direction to move the guidewire 20 from a retracted position, illustrated, for example, in FIG. 1A, to an advanced position, illustrated, for example, in FIG. 1B. In some embodiments, the guidewire 20 may extend beyond a distal tip of the introducer needle 18 when the guidewire 20 is in the advanced position. In some embodiments, the guidewire 20 may include a coil-tip, a blunt tip, a soft tip, a round tip, or other geometry that may reduce vein damage and complication from needle 18 and/or guidewire 20 advancement during placement of the catheter 14. In some embodiments, the guidewire 20 may be constructed of one or more materials. In some embodiments, the guidewire 20 may include one or more geometries that may facilitate localized stiffness and/or other properties of the guidewire 20.

In some embodiments, the introducer needle 18 may include a proximal end, a distal tip 26, and a needle lumen 28 extending between the proximal end of the introducer needle 18 and the distal tip 26. In some embodiments, the proximal end of the introducer needle 18 may be secured within the housing 16. For example, the proximal end of the introducer needle 18 may be coupled to a needle hub 30, which may be disposed within the housing 16. In some embodiments, the needle hub 30 may be part of and/or integrally formed with the housing 16. In some embodiments, the guidewire 20 may be disposed within the needle lumen 28. In some embodiments, the guidewire 20 may move within the needle lumen 28 when the guidewire 20 is moved from the retracted position to the advanced position. In some embodiments, a distal end 32 of the guidewire 20 may be disposed in the needle lumen 28 when the guidewire 20 is in the retracted position.

In some embodiments, the IV catheter system 10 may include an integrated catheter adapter 12. In further detail, in some embodiments, the IV catheter system 10 may include a catheter adapter 12 having an integrated extension tube 34, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System.

Figure 2A:
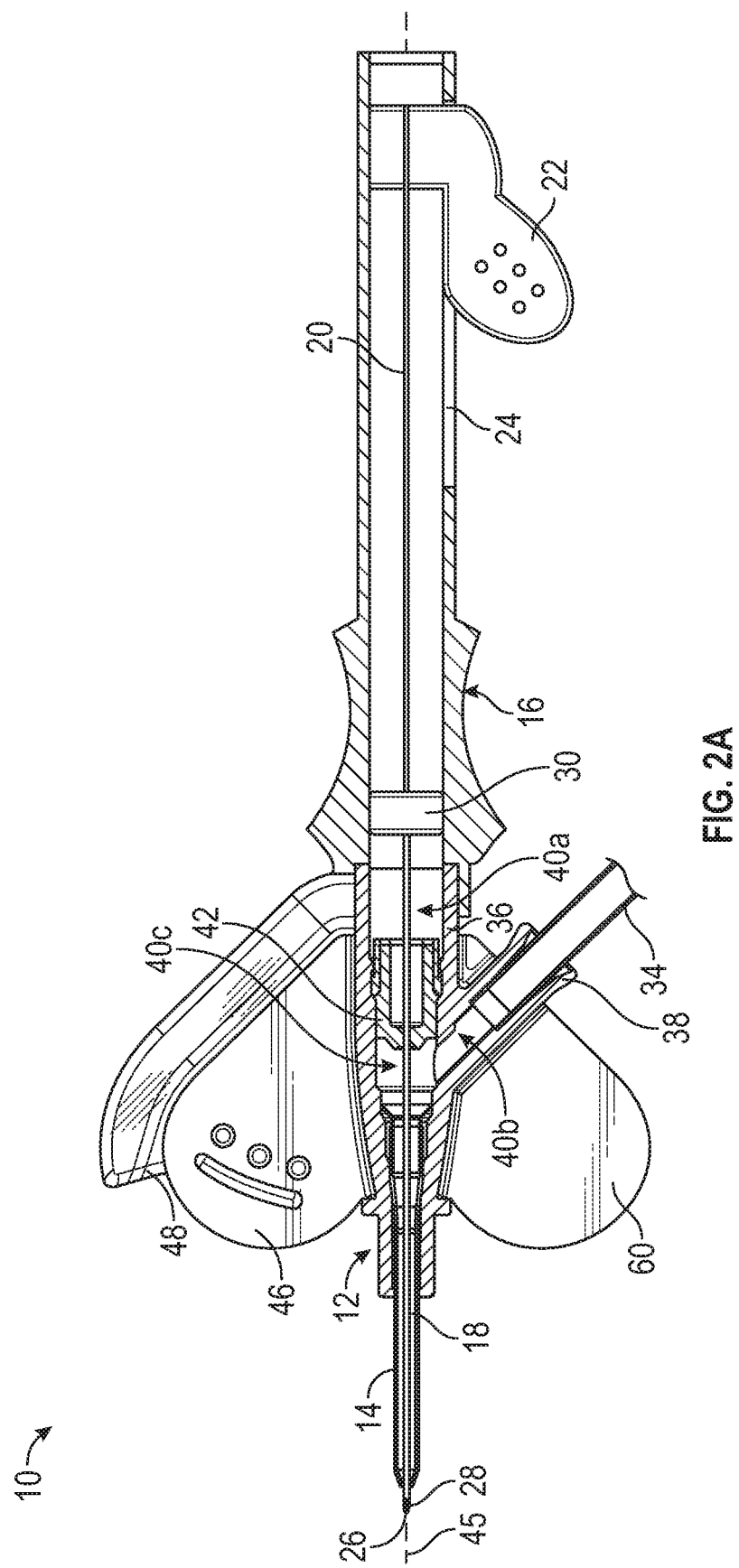
FIG. 2A is a cross-sectional view of the example IV catheter system of FIG. 1A, illustrating the guidewire in the retracted position, according to some embodiments.
Figure 2B:
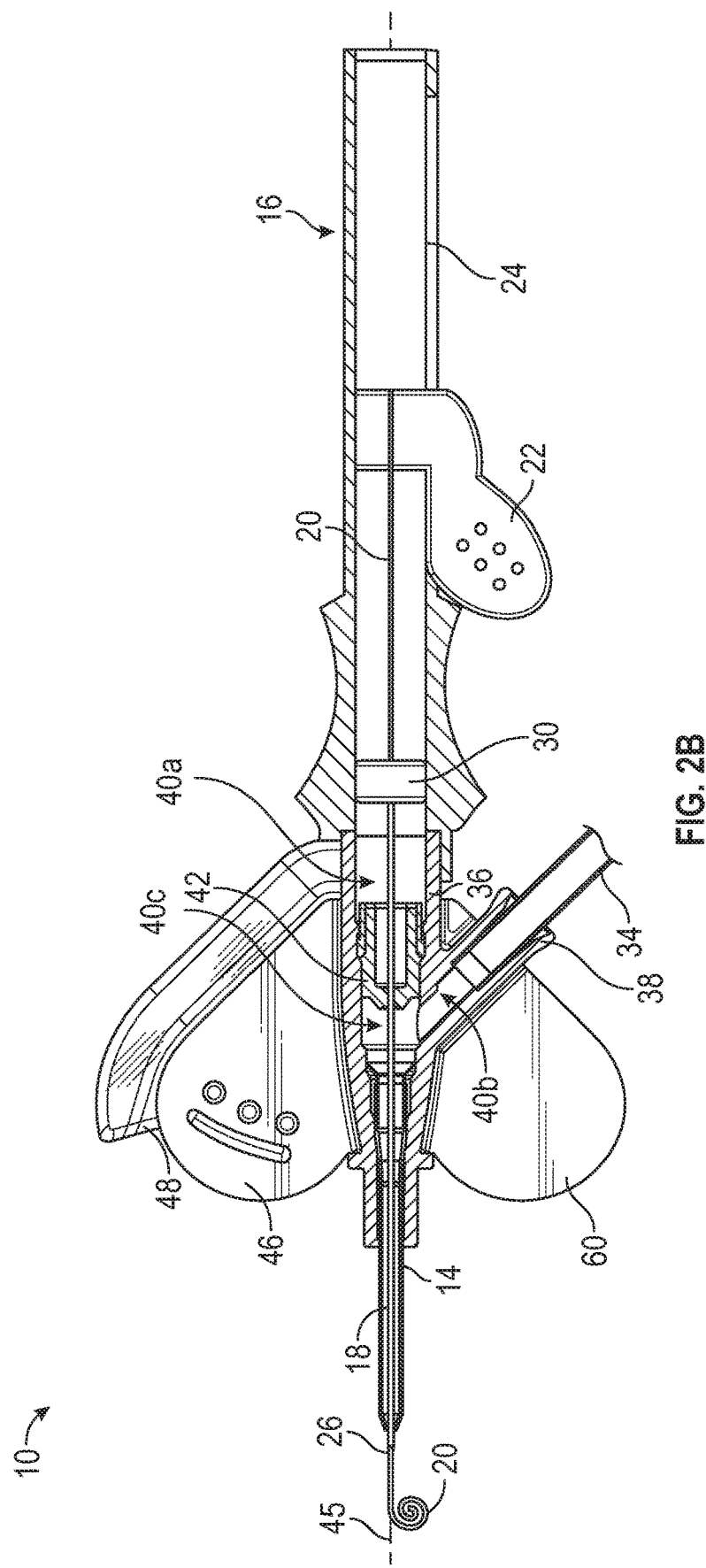
FIG. 2B is a cross-sectional view of the example IV catheter system of FIG. 1A, illustrating the guidewire in the advanced position, according to some embodiments.

In these and other embodiments, the catheter adapter 12 may include a first port 36 and a second port 38. Referring now to FIGS. 2A-2B, in some embodiments, a lumen 40 of the catheter adapter may include a first lumen 40a, a second lumen 40b, and a common lumen 40c. In some embodiments, the first port 36 may form the first lumen 40a and/or the second port 38 may form the second lumen 40b. In some embodiments, the first lumen 40a and the second lumen 40b may join at the common lumen 40c. In some embodiments, the first lumen 40a may be generally aligned with the common lumen 40c and/or the second port 38 may correspond to a side port.

In some embodiments, the catheter adapter may include a septum 42. In some embodiments, the septum 42 may be a low-drag septum. The septum 42 may include one or more pieces. In an integrated catheter adapter, the septum 42 may be disposed within the first lumen, which may correspond to a "needle channel." In some embodiments, the guidewire advancement element 22 may be moveable along the slot 24 in the distal direction to advance the guidewire 20 through the septum 42. In these and other embodiments, the guidewire 20 may be disposed within the introducer needle 18.

In some embodiments, the septum 42 may close off the first lumen 40a from an external environment surrounding the catheter adapter 12. Thus, in some embodiments, the septum 42 may at least substantially seal the first port 40a and prevent fluid from exiting the catheter adapter 12 through the first port 36. In some embodiments, a fluid pathway of the IV catheter system 10 during fluid infusion and/or blood withdrawal may extend through the second port 38 and not the first port 36. In some embodiments, a majority or substantially all of the fluid and/or the blood may flow through the second port 38 and not the first port 36.

In some embodiments, the second port 38 may be coupled to an extension tube 34. In some embodiments, the second lumen 40b of the catheter adapter 12 may be connectable to blood withdrawal or infusion means 44 via the extension tube 34 that may extend from the second port 38 of the catheter adapter 12.

In some embodiments, the slot 24 may be disposed in any portion of the housing. In some embodiments, the slot 24 may be disposed in a left or right side of the housing 16. In some embodiments, the slot 24 may be disposed in a top or bottom of the housing. In some embodiments, the left and right sides of the IV catheter system 10 may be divided by a central plane 45. In some embodiments, the slot 24 may be aligned with the central plane 45 of the IV catheter system 10.

In some embodiments, the catheter adapter 12 may include a wing 46 extending outwardly from a right side of a body of the catheter adapter 12. In these and other embodiments, the guidewire advancement element 22 may be disposed on a left side of the IV catheter system 10 and/or aligned with the central plane 45, which may facilitate access to the guidewire advancement element 22 by the user when the user also grips the wing 46.

In some embodiments, the IV catheter system 10 may include a grip 48, which may extend outwardly from a body of the housing 16. In some embodiments, the grip 48 may extend through the slot 24 or another slot in the housing 16. In some embodiments, the grip 48 may be disposed in various locations with respect to the IV catheter system 10, which may facilitate access to the grip 48 by the user. In some embodiments, the grip 48 may include a shape that generally corresponds to a shape of the wing 46. In some embodiments, a ridge on an upper surface of the grip 48 may prevent proximal movement of the catheter adapter 12 with respect to the housing 16. In some embodiments, the IV catheter system 10 may not include the wing 46. In some embodiments, the grip 48 may be disposed on a right side of the IV catheter system 10. In these and other embodiments, the guidewire advancement element 22 may be disposed on a left side of the IV catheter system 10 and/or aligned with the central plane 45, which may facilitate access to the guidewire advancement element 22 by the user when the user also grips the grip 48.

Figure 1C:
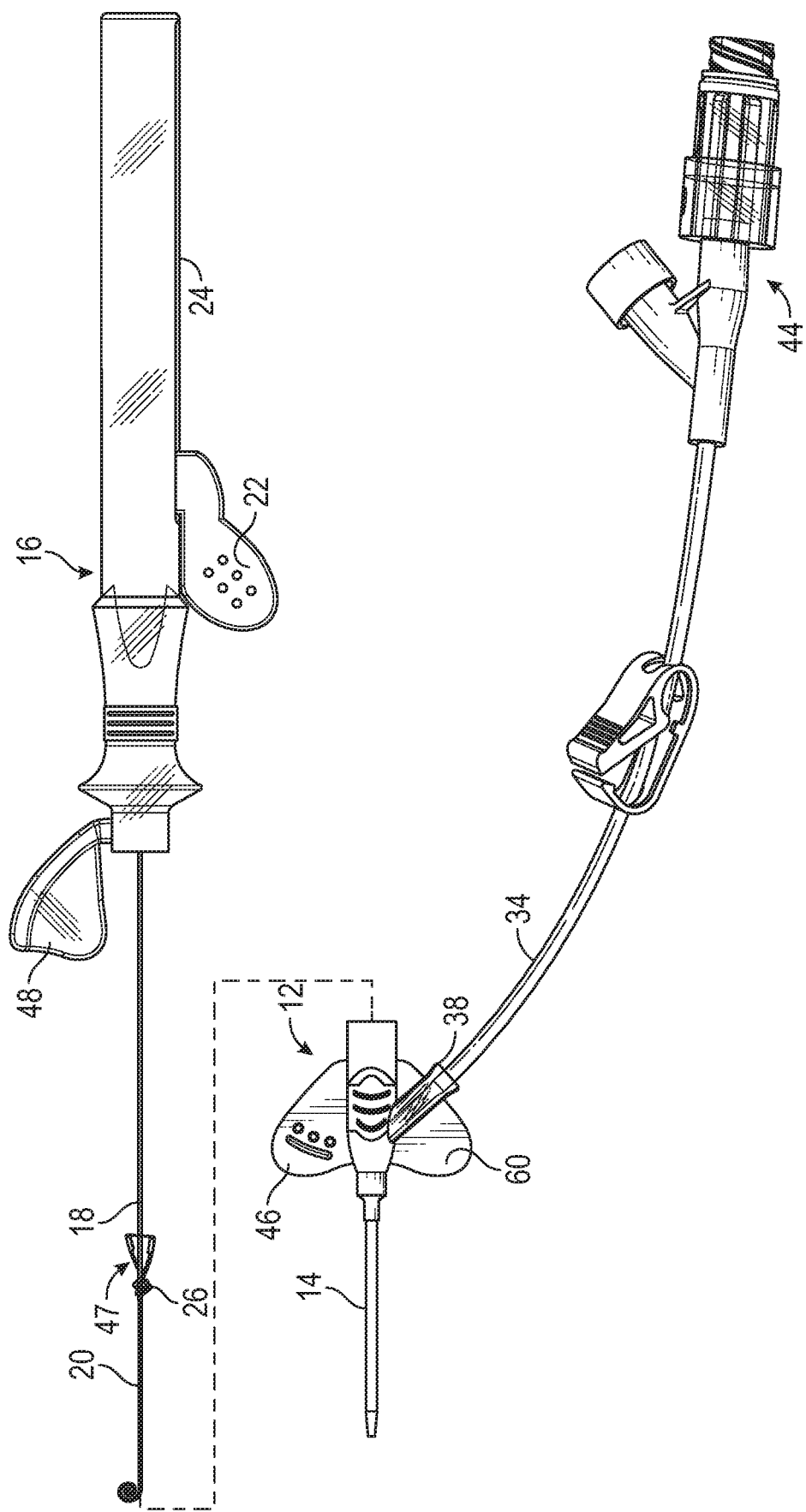
FIG. 1C is a top view of an the IV catheter system of FIG. 1A, illustrating an example housing removed from an example catheter adapter, according to some embodiments.

In some embodiments, the IV catheter system 10 may include a needle safety mechanism, examples of which will be discussed with respect to FIGS. 1C-1E, 3D, 4, and 5A-9. In some embodiments, the IV catheter system 10 may not include a needle safety or shielding mechanism. As illustrated in FIG. 1C, in some embodiments, the housing 16 may be uncoupled or removed from the catheter adapter 12 when the guidewire 20 is in the advanced position and/or the introducer needle 18 is in an advanced or insertion position.

Figure 1D:
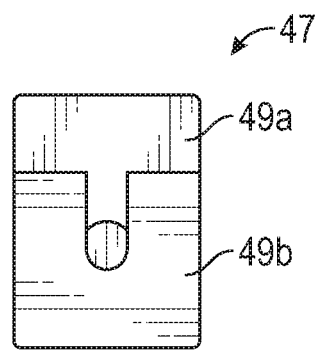
FIG. 1D is distal end view of an example needle shielding mechanism that may be used with the IV catheter system of FIG. 1A, according to some embodiments.
Figure 1E:
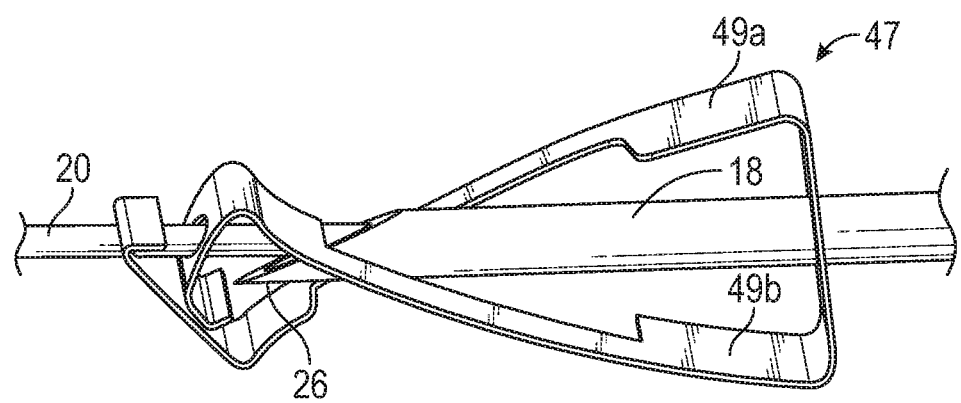
FIG. 1E is an upper perspective view of the needle shielding mechanism of FIG. 1D, according to some embodiments.

Referring now to FIGS. 1C-1E, in some embodiments, the IV catheter system 10 may include a needle safety mechanism 47. In some embodiments, the needle safety mechanism 47 may include a spring clip, which may include a resilient first arm 49a and a resilient second arm 49b. In some embodiments, the needle safety mechanism 47 may include any suitable clip or needle safety mechanism. In some embodiments, proximal ends of the first arm 49a and the second arm 49b may join at a proximal wall, which may include an opening sized and configured to slidably receive a proximal end of the introducer needle 18 as the introducer needle 18 is advanced in a distal direction. In some embodiments, a needle feature or bump (not illustrated) may prevent the distal tip 26 of the introducer needle 18 from being withdrawn proximally through the opening as a diameter of the needle feature or bump may be larger than a diameter of the opening.

In some embodiments, distal ends of the first arm 49a and the second arm 49b may be curved and/or include a lip. In some embodiments, when the introducer needle 18 is in the insertion position, ready for insertion into the patient, the introducer needle 18 may be disposed between the distal end of the first arm 49a and the distal end of the second arm 49b, biasing the first and second arms 49a,b outwardly. In some embodiments, when the first and second arms 49a,b are biased outwardly they may engage an inner wall of the catheter adapter 12, securing the needle safety mechanism 47 within the catheter adapter 12. In response to withdrawal of the introducer needle 18 from the patient and movement of the distal tip 26 proximal to the distal ends of the first and second arms 49a,49b, the distal ends of the first and second arms 49a, 49b may move closer to each other and/or overlap, which may release the needle safety mechanism 47 from the catheter adapter 12 and prevent the introducer needle 18 from moving in a distal direction beyond the needle safety mechanism 47, as illustrated in FIG. 1E, for example.

In some embodiments, the distal end of the first arm 49a and/or the distal end of the second arm 49b may include an aperture sized and configured to receive the guidewire 20. In some embodiments, a diameter of the aperture may be less than the diameter of the introducer needle 18, which may prevent the introducer needle 18 from moving distally through the aperture in the shielded position.

Figure 3A:
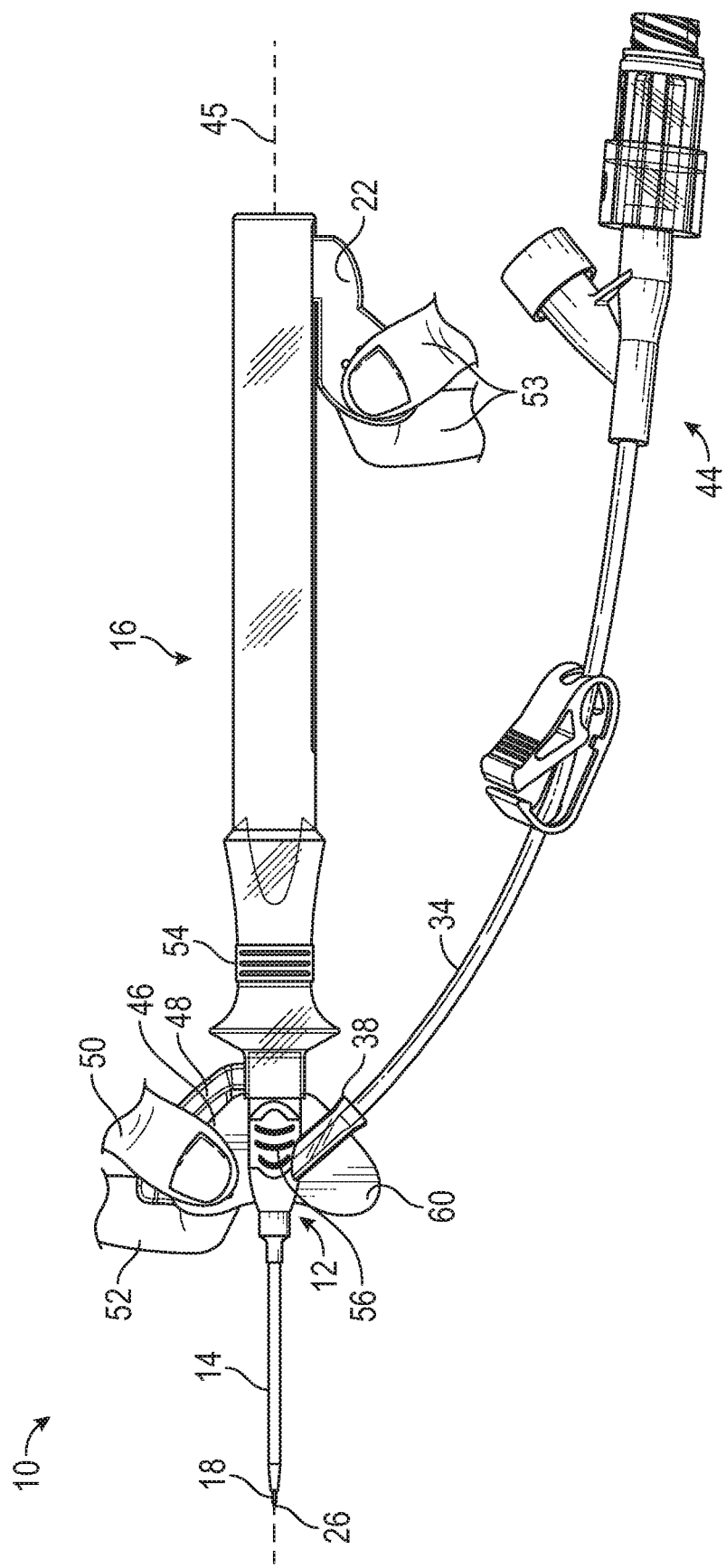
FIG. 3A is a top view of the example IV catheter system of FIG. 1A, illustrating a user gripping the IV catheter system according to an example nested winged grip, according to some embodiments.
Figure 3B:
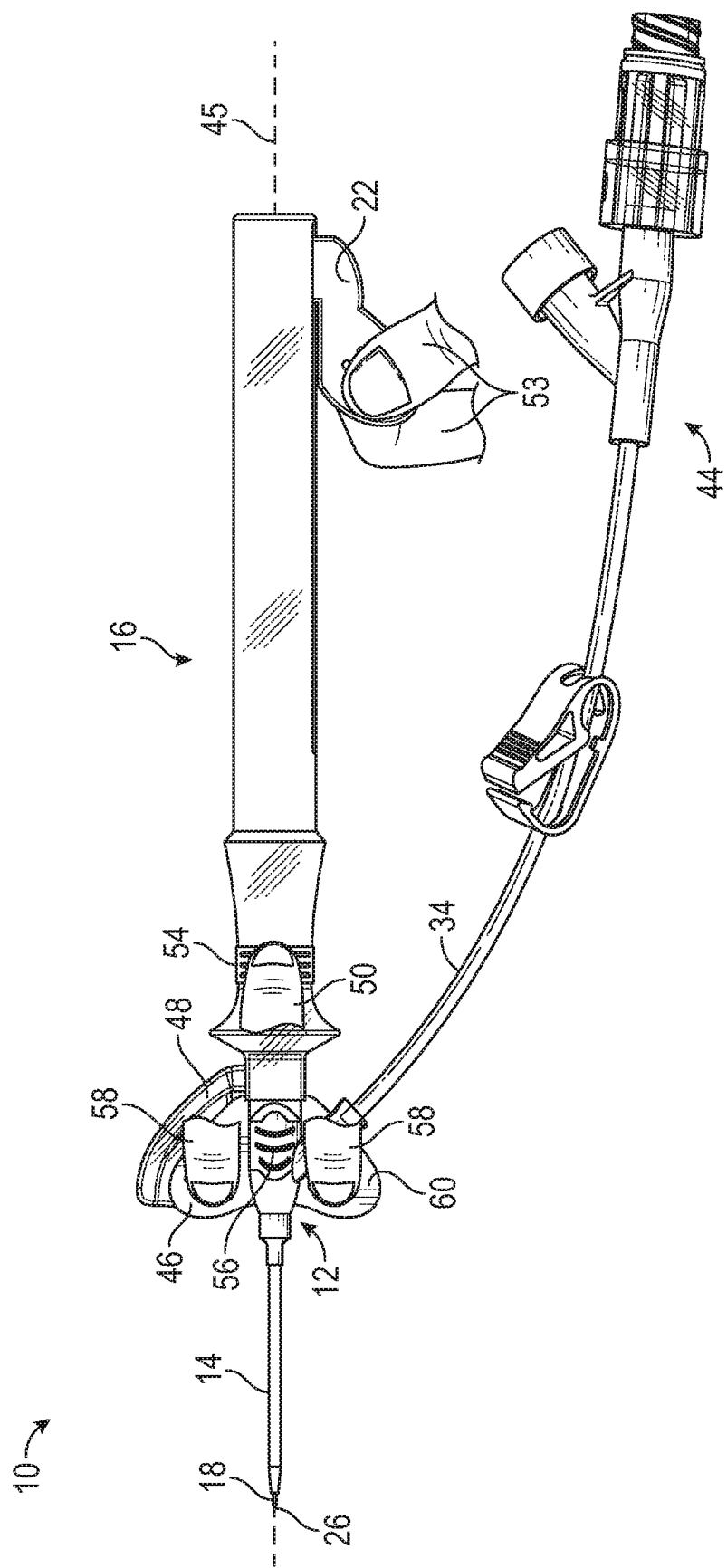
FIG. 3B is a top view of the example IV catheter system of FIG. 1A, illustrating the user gripping the IV catheter system according to an example ported grip, according to some embodiments.
Figure 3C:
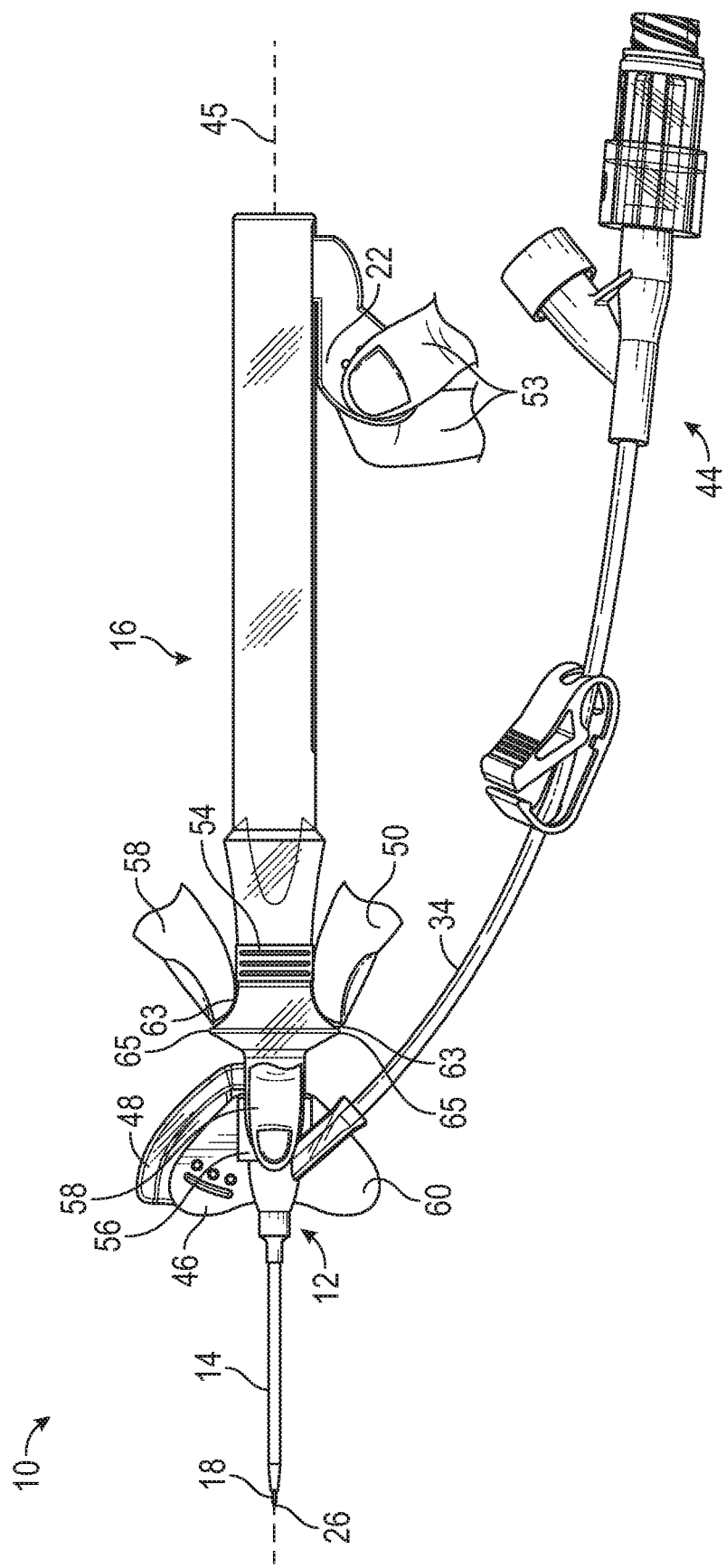
FIG. 3C is a top view of the example IV catheter system of FIG. 1A, illustrating the user gripping the IV catheter system according to an example central grip, according to some embodiments.

Referring now to FIGS. 3A-3C, in some embodiments, the housing 16 may include a thumb tab 54. Additionally or alternatively, in some embodiments, the catheter adapter 12 may include a finger push or grip tab 56. In some embodiments, the thumb tab 54 and/or the finger push or grip tab 56 may be laterally offset from a portion of the grip 48 that may be gripped by the user, such as, for example, a winged portion of the grip 48, which may facilitate access to the guidewire advancement element 22 by the user. In some embodiments, the thumb tab 54 and/or the finger push or grip tab 56 may be aligned with the central plane 45 of the IV catheter system 10 and/or disposed on a top of the catheter adapter 12 and/or the housing 16, as illustrated, for example, in FIGS. 3A-3C.

As illustrated in FIG. 3A, in some embodiments, the grip 48 may be positioned directly beneath the wing 46 so that the wing 46 and the grip 48 may be sandwiched between a thumb 50 of a first hand and an index finger 52 of the first hand of the user during insertion of the catheter 14 into the vasculature of the patient via a nested winged grip. In these embodiments, the user may easily withdraw the housing 16 from the catheter adapter 12 by simply sliding the index finger 52 proximally with respect to the thumb 50 thereby causing the grip 48 to slide proximally away from the wing 46. In some embodiments, the grip 48 may be configured to be positioned above or adjacent to the wing 46.

In some embodiments, the guidewire advancement element 22 may centrally located on the housing 16 and aligned with the central plane 45 of the IV catheter system 10. In these and other embodiments, the guidewire advancement element 22 may be aligned with the thumb tab 54 and/or the finger push or grip tab 56. In some embodiments, the thumb tab 54 and/or the finger push or grip tab 56 may be laterally offset from the guidewire advancement element 22 to facilitate access to the guidewire advancement element 22 by the user when the user grips the IV catheter system 10 in a ported grip. As an example, the thumb tab 54 and/or the finger push or grip tab 56 may be aligned with the central plane 45, and the guidewire advancement element 22 may be disposed on a side of the housing 16, as illustrated, for example, in FIG. 3B.

In some embodiments, a particular finger 58 of the first hand of the user may grip the wing 46 at a same time as another particular finger 58 of the first hand grips another wing 60 and the thumb 50 of the first hand grips the thumb tab 54, as illustrated, for example, in FIG. 3B. In some embodiments, the particular finger 58 may include a middle finger of the first hand of the user or another finger of the first hand of the user. In some embodiments, the other particular finger 58 may include the index finger 52 of the first hand of the user, the middle finger of the first hand of the user, or another finger of the first hand of the user. In some embodiments, the IV catheter system 10 may not include the wing 46 and the particular finger 58 may contact an upper surface of the grip 58, gripping the grip 58. In some embodiments, the user may grip the IV catheter system 10 in the ported grip, or another grip, with a first hand, such as, for example, the right hand of the user, and grip and/or move the guidewire advancement element 22 with a second hand 53, such as, for example, the left hand.

FIG. 3C illustrates a particular finger 58, for example, the middle finger of the first hand, and the thumb 50 of the first hand gripping the IV catheter system 10 in a central grip, allowing another particular finger 58 of the first hand, for example, the index finger 52, to apply distally directed pressure to the finger push or grip tab 56 to advance the catheter adapter distally relative to the introducer needle, according to some embodiments. In some embodiments, the housing 16 may further include one or more guard features 61. In some embodiments, the guard features 61 may provide a physical barrier between opposing digits of the user and the catheter adapter 12. In some embodiments, each of the guard features 61 may include an outward, exponential curve 63. In some embodiments, a peak 65 of the exponential curve 63 may be an outermost surface of the guard feature 61. In other embodiments, the guard features 61 may include any physical barrier to prevent a grip of the user from extending beyond the housing 16 to contact the catheter adapter 12. In some embodiments, the guard features 40 may be disposed proximal to the grip 48.

FIG. 3D illustrates another example IV catheter system 62, according to some embodiments. In some embodiments, the IV catheter system 62 may not include the grip 48. FIG. 3D illustrates the user gripping the IV catheter system 62 according to a winged grip in which the wing 46 is pinched between the thumb 50 of the first hand and the index finger 52 of the first hand of the user.

FIG. 3D also illustrates an example safety mechanism. In further detail, in some embodiments, a push button 64 may release a spring and allow the introducer needle 18 and/or the guidewire 20 to retract within the housing 16. The user may decide when to activate the push button 64. In some embodiments, the IV catheter system 62 may include or correspond to the IV catheter system 10 of FIGS. 1-3C. In further detail, in some embodiments, the IV catheter system 10 may include one or more features of the IV catheter system 62 and/or the IV catheter system 62 may include one or more of the features of the IV catheter system 10. For example, the IV catheter system 10 may include the push button 64 and related safety mechanism.

FIG. 4 illustrates another IV catheter system 66 having the guidewire 20 in the retracted position, according to some embodiments. In some embodiments, the IV catheter system 66 may be non-integrated. In some embodiments, the IV catheter system 66 may include or correspond to the IV catheter system 10 of FIGS. 1-3C and/or the IV catheter system 62 of FIG. 3D. In further detail, in some embodiments, the IV catheter system 10 and/or the IV catheter system 62 may include one or more features of the IV catheter system 66. In some embodiments, the IV catheter system 66 may include one or more features of the IV catheter system 10 and/or the IV catheter system 62.

Referring now to FIGS. 5A-9, another IV catheter system 68 is illustrated, according to some embodiments. In some embodiments, in response to movement of the guidewire advancement element 22 along the slot 24 in the distal direction to move the guidewire 20 from the retracted position to the advanced position, the guidewire advancement element 22 may couple to the grip 48. In some embodiments, the guidewire advancement element 22 may couple to the grip 48 via an interference fit or any another suitable coupling mechanism.

In some embodiments, in response to movement of the guidewire advancement element 22 along the slot 24 in the distal direction to move the guidewire 20 from the retracted position to the advanced position, the guidewire advancement element 22 may not couple to the grip 48.

In some embodiments, the introducer needle 18 may be coupled to the grip 48 and/or extend through the grip 48. In particular, in some embodiments, the introducer needle may be coupled to a portion of the grip 48 disposed within the housing 16, which may include or correspond to the needle hub 30.

In some embodiments, the guidewire advancement element 22 and/or the grip 48 may be moveable along the slot 24 in the distal direction and/or the proximal direction. In some embodiments, in response to movement of the guidewire advancement element 22 and/or the grip 48 along the slot 24 in the proximal direction, the guidewire 20 and the introducer needle 18 may move towards the proximal end of the housing 16. In some embodiments, in response to movement of the guidewire advancement element 22 and/or the grip 48 along the slot 24 in the proximal direction, the introducer needle 18 may be shielded within the housing 16 such that the distal tip 26 of the introducer needle 18 is contained within the housing 16. Additionally or alternatively, in some embodiments, in response to movement of the guidewire advancement element 22 and/or the grip 48 along the slot 24 in the proximal direction, the guidewire 20 may be shielded within the housing 16 such that the distal end 32 of the guidewire 20 is contained within the housing 16.

In some embodiments, the housing 16 may include the other slot (not illustrated), which may be disposed in any portion of the housing 16. In some embodiments, the other slot may be disposed in a top or bottom of the housing 16. In some embodiments, the other slot may be disposed in the left or right side of the housing 16. In some embodiments, the other slot may be aligned with the central plane 45 of the IV catheter system 68.

In some embodiments, the grip 48 may be moveable along the slot 24 and/or the other slot 24 in the distal and/or proximal direction. In some embodiments, in response to movement of the grip 48 along the other slot 24 in the proximal direction, the guidewire 20, the guidewire advancement element 22, and the introducer needle 18 may move proximally within the housing 16.

In some embodiments, the grip 48 may not be coupled to the guidewire advancement element 22, however, in response to movement of the grip 48 along the slot 24 or the other slot in the proximal direction, the grip 48 may move the guidewire advancement element 22 proximally. For example, in response to movement of the grip 48 along the slot 24 or the other slot in the proximal direction, the grip 48 may contact a distal end of the guidewire advancement element 22 and drive movement the guidewire advancement 22 element proximally.

In some embodiments, in response to movement of the grip 48 along the other slot in the proximal direction, the introducer needle 18 may be shielded within the housing 16 such that the distal tip 26 of the introducer needle 18 is contained within the housing 16 and/or a portion of the grip 48 may be shielded within the housing 16. Additionally or alternatively, in some embodiments, in response to movement of the grip 48 along the other slot in the proximal direction, the guidewire 20 may be shielded within the housing 16 such that a distal end 32 of the guidewire 20 is contained within the housing 16.

In some embodiments, in response to shielding of the distal tip 26 of the introducer needle 18 within the housing 16 and/or shielding of the distal end 32 of the guidewire 20 within the housing 16, the housing 16 may be configured to separate and/or uncouple from the catheter adapter 12. In further detail, in some embodiments, in response to shielding of the distal tip 26 of the introducer needle 18 and/or shielding of the distal end 32 of the guidewire 20 within the housing 16, a coupling mechanism between the catheter adapter 12 and the housing 16 may be released, automatically and/or by the user. For example, the coupling mechanism may include a latch mechanism or any other suitable type of coupling mechanism. In some embodiments, the user may twist or rotate an outer sleeve of the housing 16 with respect to an inner sleeve of the housing 16 and the catheter adapter 12, which may uncouple the catheter adapter 12 from the housing 16.

In some embodiments, when the outer sleeve of the housing 16 is rotated with respect to the inner sleeve of the housing 16 and the catheter adapter 12, the catheter advancement element 22 and/or the grip 38 may rotate through a gap 72 in the inner sleeve. In some embodiments, the gap 72 may be part of the slot 24 of the housing 16. In some embodiments, the gap 72 may allow the rotation of the outer sleeve of the housing 16 with respect to the inner sleeve of the housing 16. In some embodiments, rotation of the outer sleeve of the housing 16 with respect to the inner housing and the catheter adapter 12 may remove a protruding feature of the outer housing from a slot 74 of the catheter adapter, illustrated, for example, in FIG. 9, freeing the housing 26 from the catheter adapter 12. In these and other embodiments, the housing 16 may be removed from the catheter adapter 12 and/or disposed of.

In some embodiments, the guidewire advancement element 22 may have a variety of shapes and sizes. In some embodiments, the guidewire advancement element 22 may at least partially wrap around the housing 16, as illustrated, for example, in FIGS. 5A-9. In some embodiments, the guidewire advancement element 22 may include one or more protrusions or ridges that may aid the user in moving the guidewire advancement element 22 in the proximal direction and/or the distal direction.

In some embodiments, the grip 48 may extend through the slot 24 in the housing 16 and the grip 48 may move along the slot 24 in the proximal direction and/or the distal direction. In some embodiments, the grip 48 may have a variety of shapes and sizes. In some embodiments, the grip 48 may include the ridge, which may generally align with an outer edge of the wing 46 when the wing is disposed on top of the grip 48 and/or the introducer needle 18 is in the insertion position, as illustrated, for example, in FIG. 5A. In some embodiments, the ridge may prevent the wing 46 from moving proximal to the grip 48.

Figure 5A:
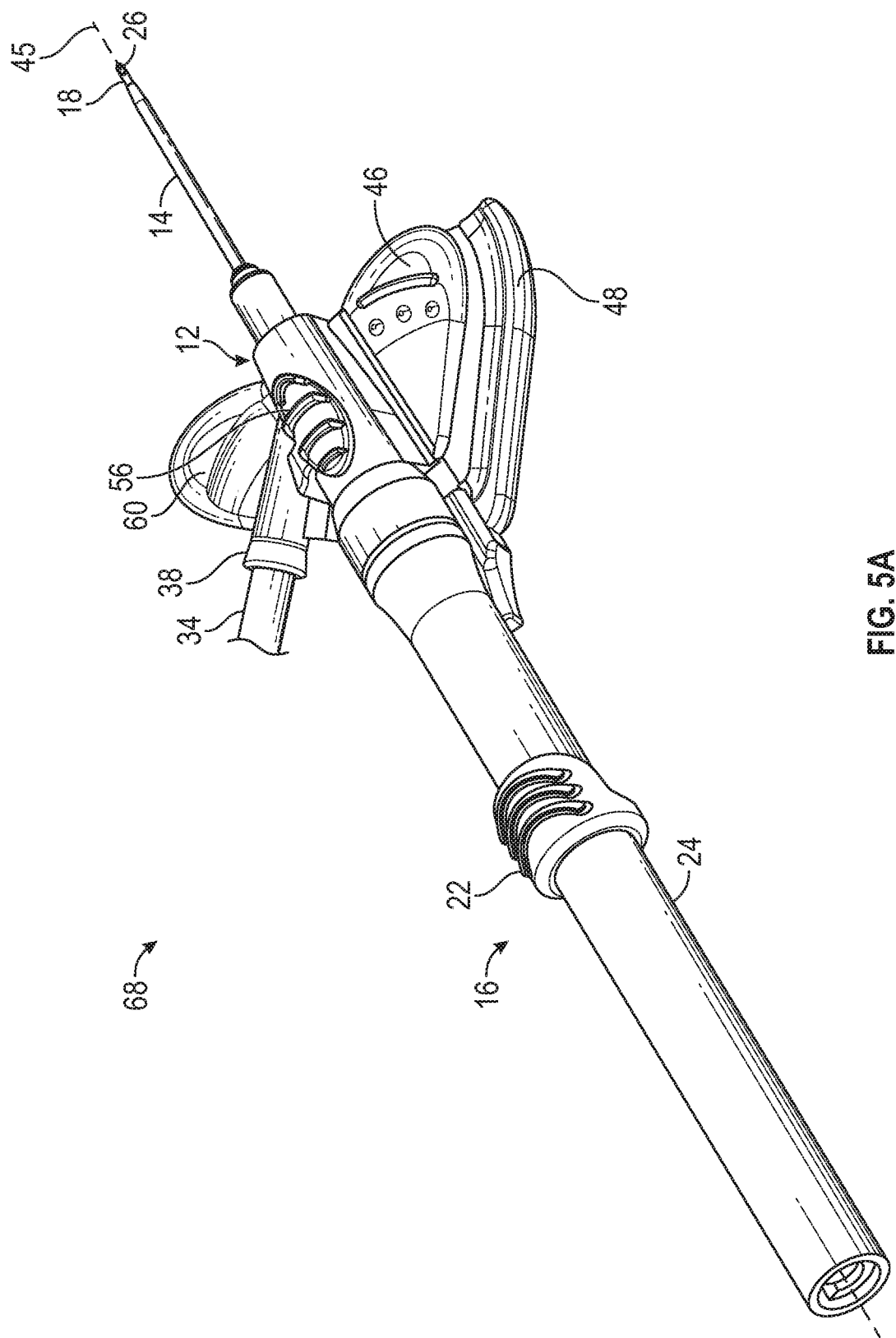
FIG. 5A is an upper perspective view of another example IV catheter system, illustrating the IV catheter system in an insertion position, according to some embodiments.
Figure 5B:
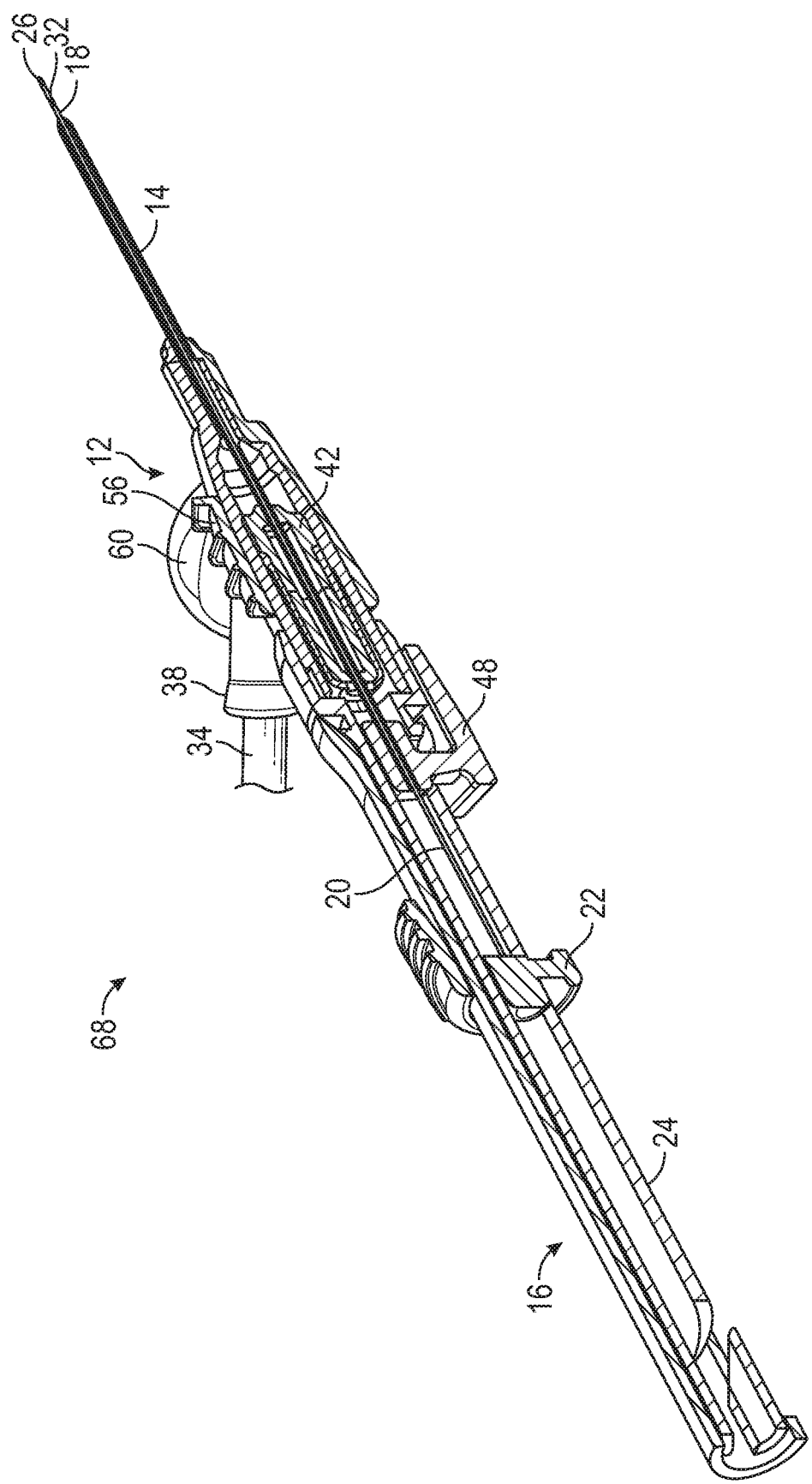
FIG. 5B is a cross-sectional view of the IV catheter system of FIG. 5A, illustrating the IV catheter system in the insertion position, according to some embodiments.

FIGS. 5A-5B illustrate the IV catheter system 68 in the insertion position, according to some embodiments. In some embodiments, the distal end 32 of the guidewire 20 may be disposed near or proximate the distal tip 26 of the introducer needle 18 when the IV catheter system 68 is in the insertion position. In some embodiments, the guidewire advancement tab 22 may be spaced apart from the grip 48 when the IV catheter system 68 is in the insertion position.

Figure 6A:
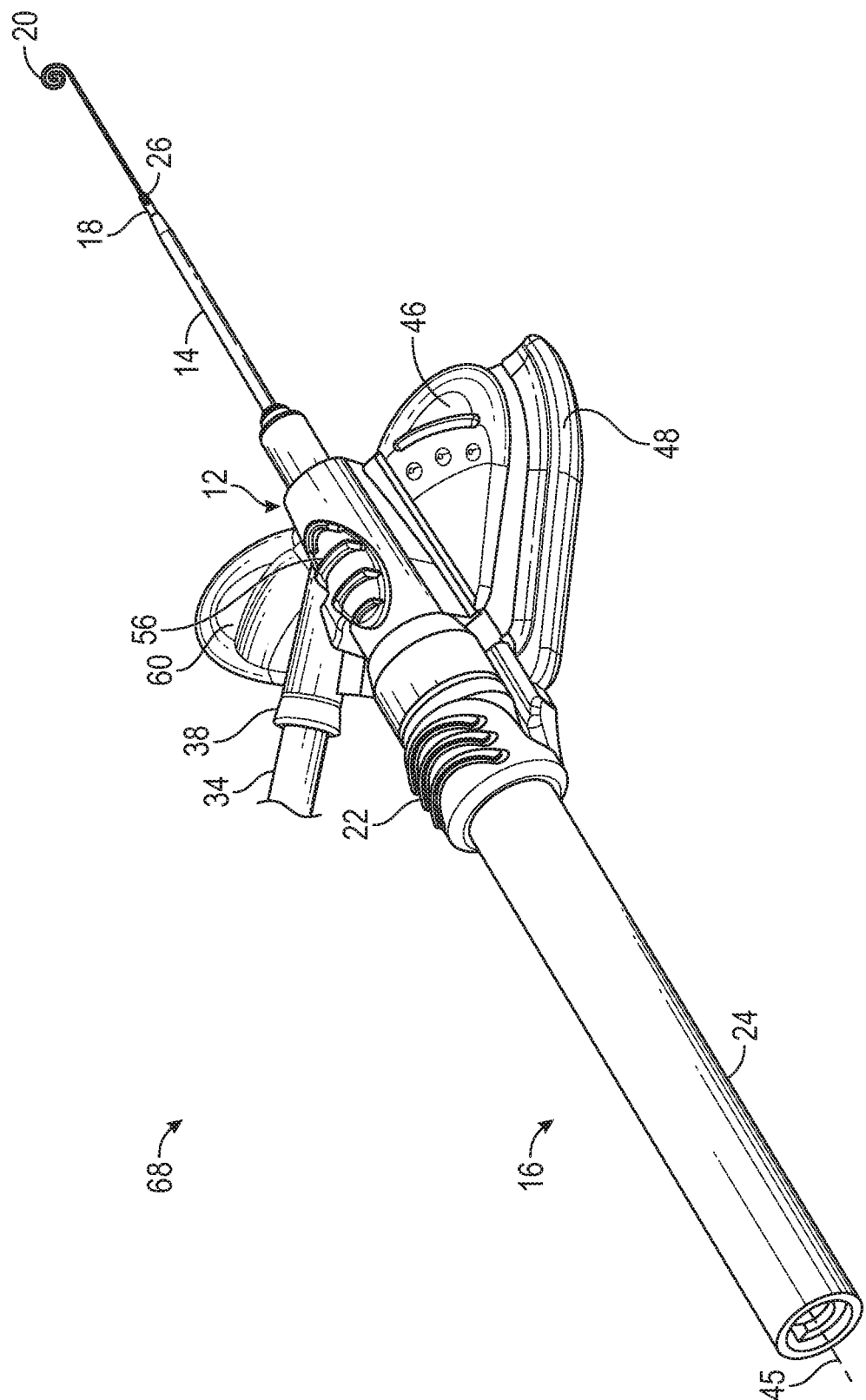
FIG. 6A is an upper perspective view of the IV catheter system of FIG. 5A, illustrating an example guidewire in the advanced position, according to some embodiments.
Figure 6B:
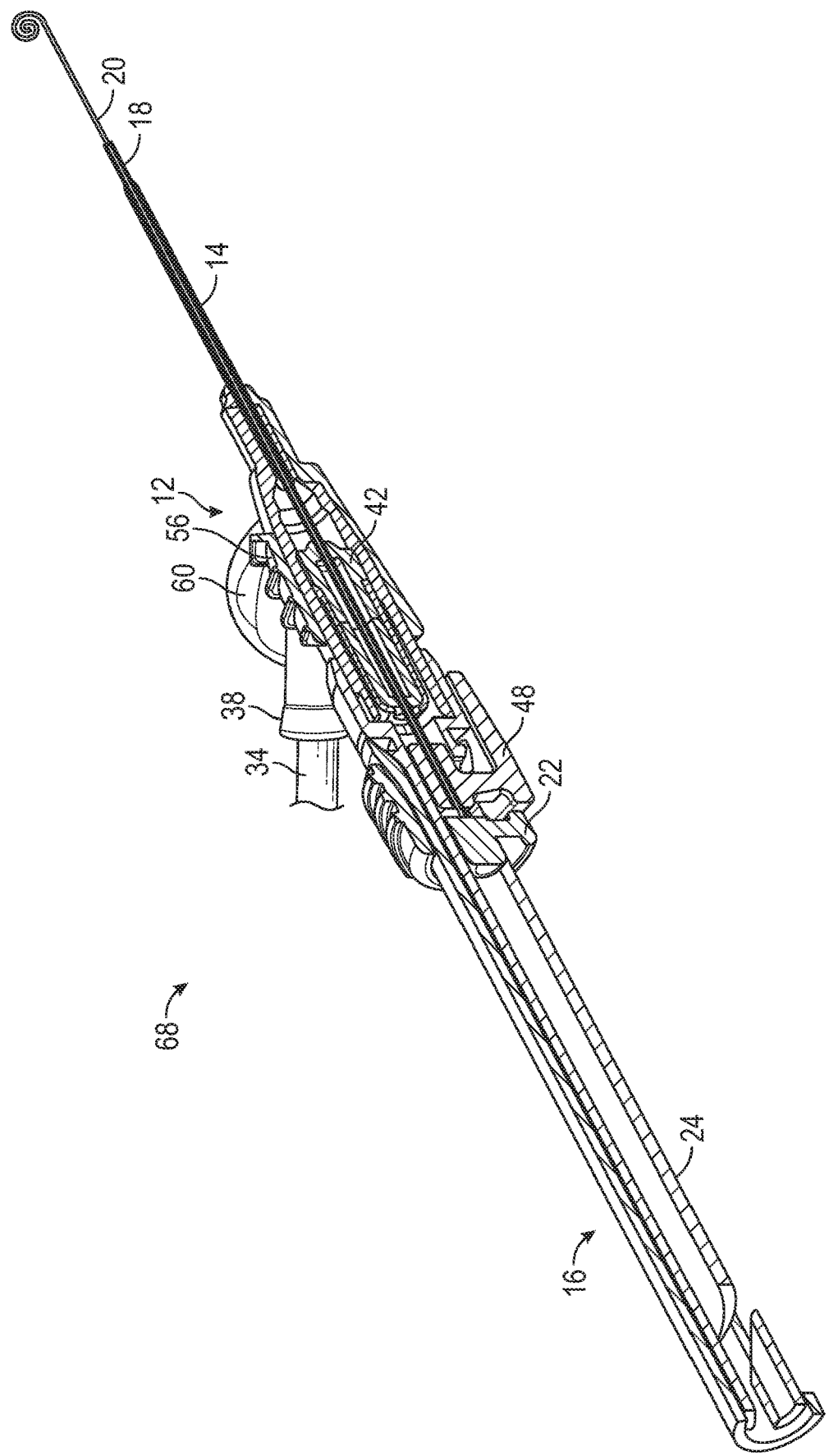
FIG. 6B is an upper perspective view of the IV catheter system of FIG. 5A, illustrating the guidewire in the advanced position, according to some embodiments.

FIGS. 6A-6B illustrate the IV catheter system 68 in the advanced position, according to some embodiments. In some embodiments, when the IV catheter system 68 is in the advanced position, the guidewire 20 may extend distal to the distal tip 26 of the introducer needle 18, which may extend distal to a distal end of the catheter 14. In some embodiments, the user may move the IV catheter system 68 to the advanced position after the IV catheter system 68 is inserted into the vasculature of the patient.

Figure 7A:
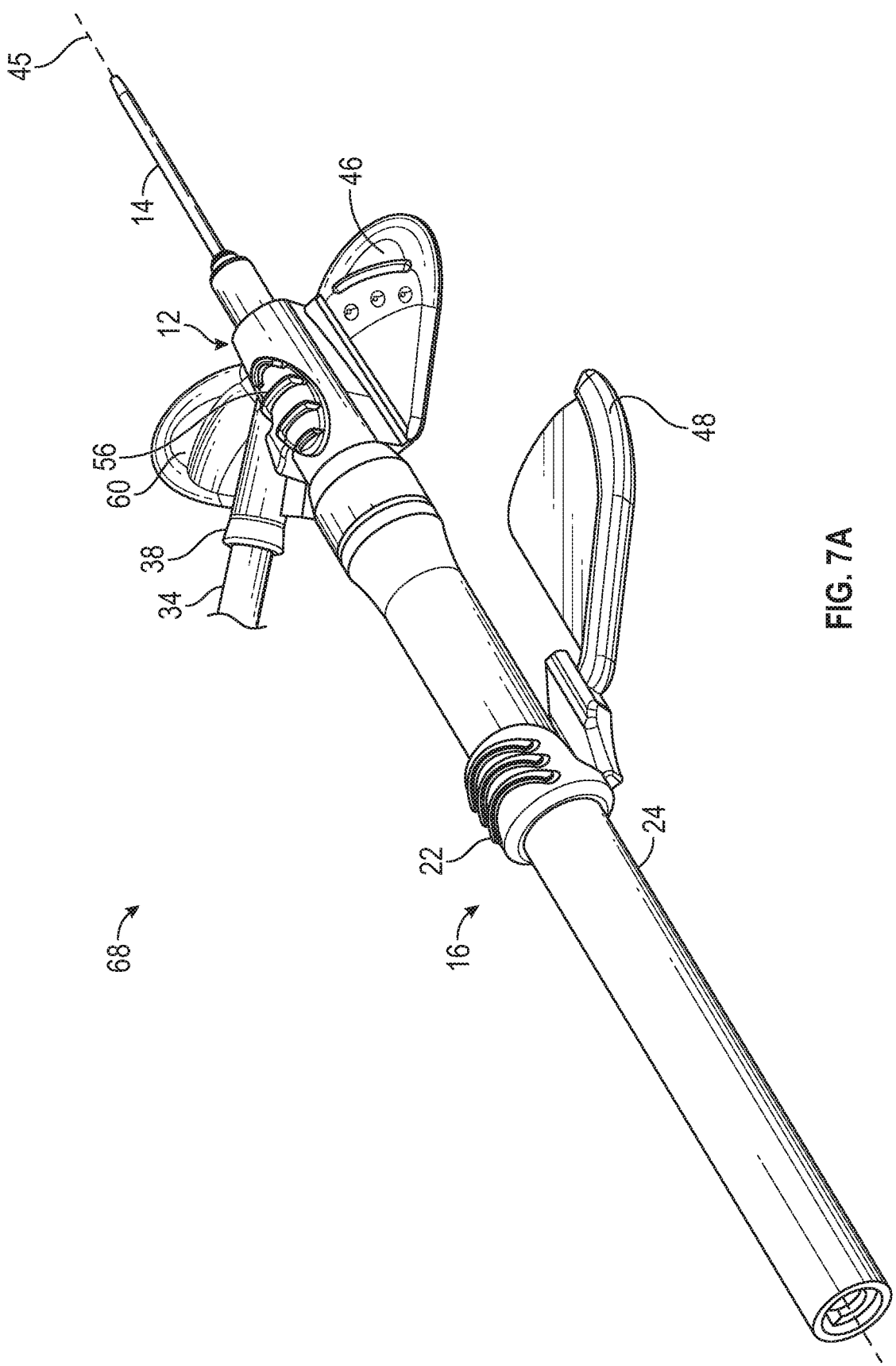
FIG. 7A is an upper perspective view of the IV catheter system of FIG. 5A, illustrating an example grip and the guidewire in a partially retracted position, according to some embodiments.
Figure 7B:
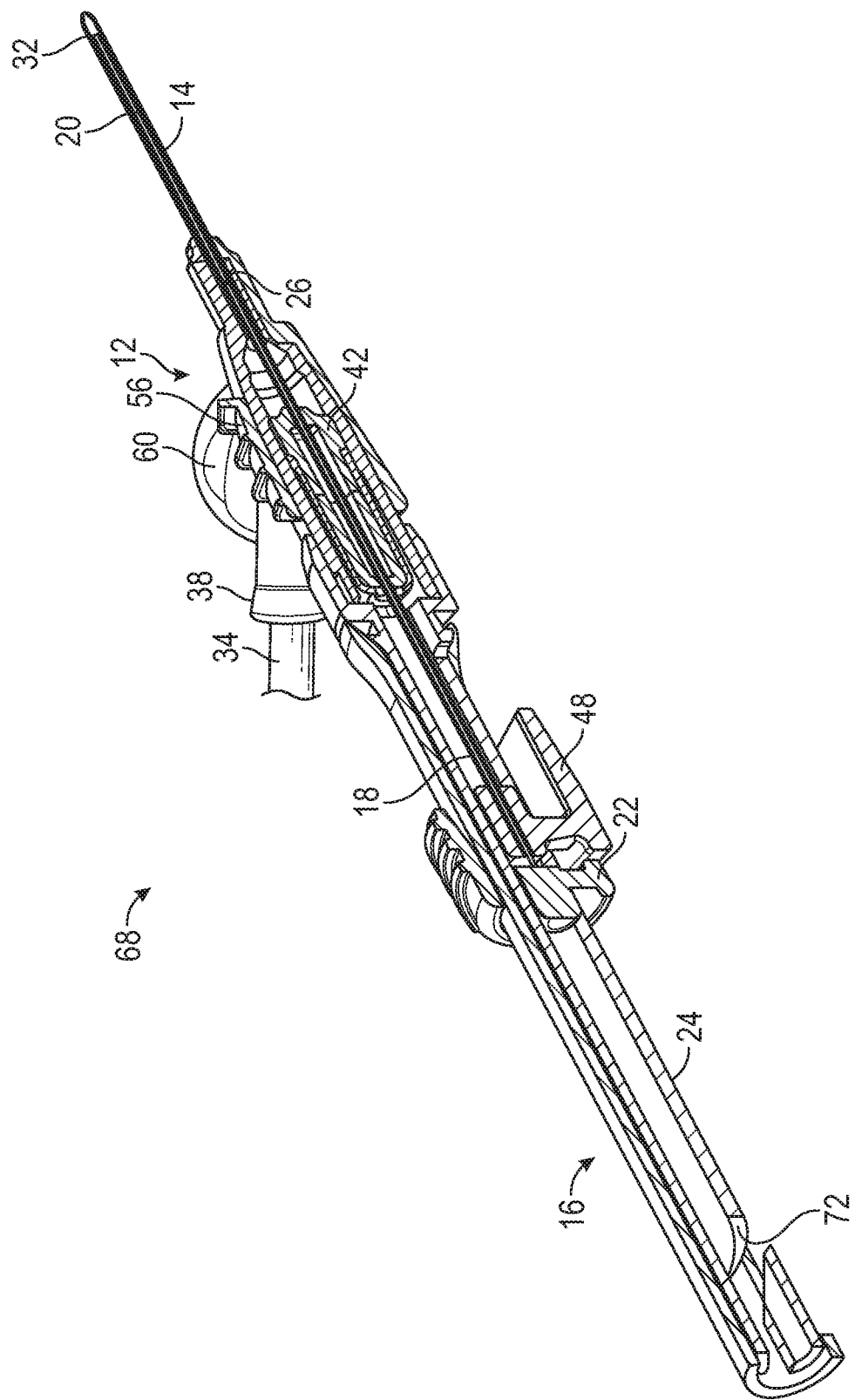
FIG. 7B is an upper perspective view of the IV catheter system of FIG. 5A, illustrating the grip and guidewire in the partially retracted position, according to some embodiments.

FIGS. 7A-7B illustrate the IV catheter system 68 in a partially retracted position, according to some embodiments. In some embodiments, the user may move the IV catheter system 68 to the partially retracted position after the IV catheter system 68 is positioned in the advanced position within the vasculature of the patient. In some embodiments, when the IV catheter system 68 is in the partially retracted position, the distal end 32 of the guidewire 20 may be disposed within the catheter 14 and/or the distal tip 26 of the introducer needle 18 may be disposed within the catheter adapter 12, although it is understood that the distal end 32 and/or the distal tip 26 may be disposed at other locations.

Figure 8A:
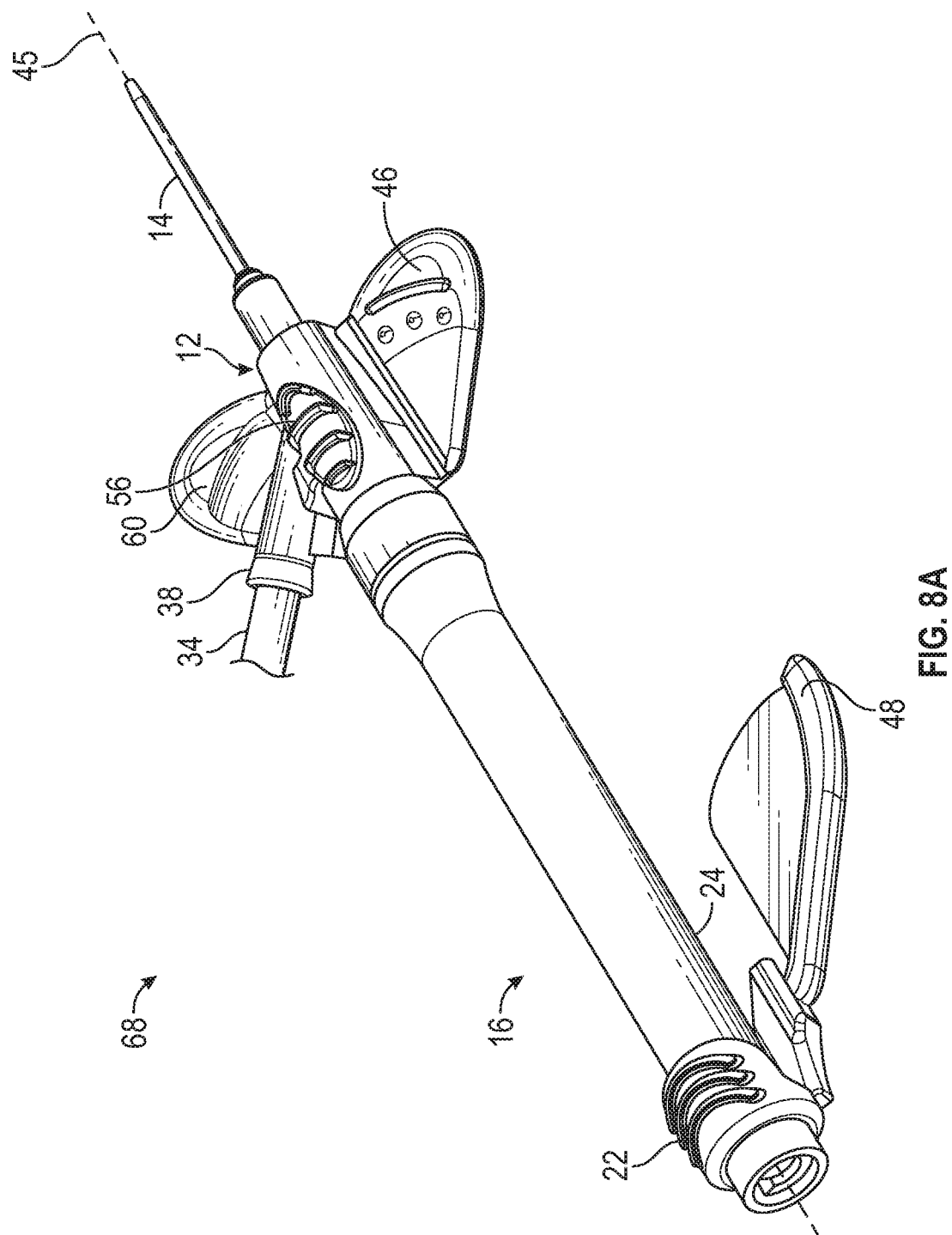
FIG. 8A is an upper perspective view of the IV catheter system of FIG. 5A, illustrating the grip and guidewire in the retracted position, according to some embodiments.
Figure 8B:
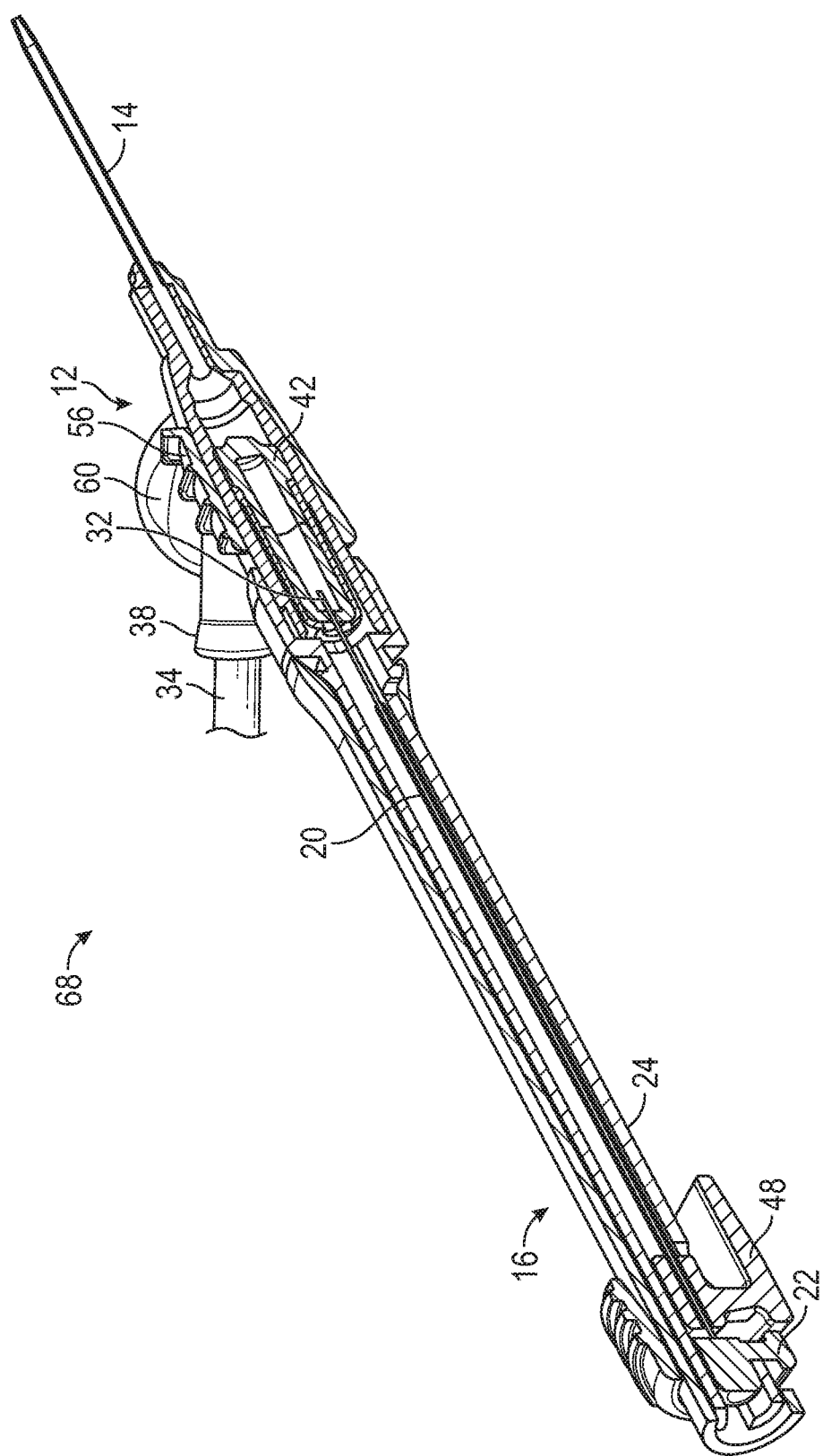
FIG. 8B is an upper perspective view of the IV catheter system of FIG. 5A, illustrating the grip and guidewire in the retracted position, according to some embodiments.
Figure 9:
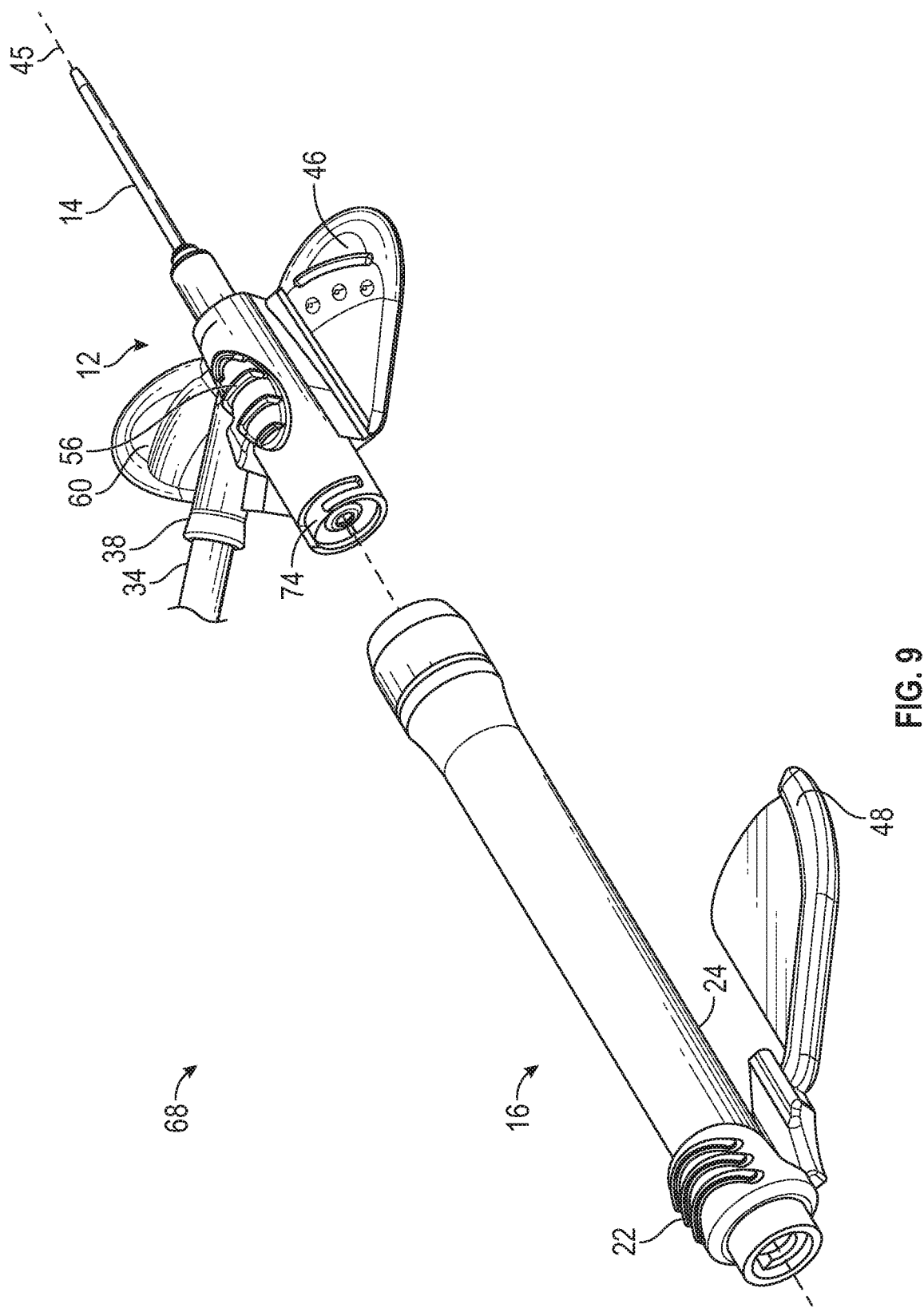
FIG. 9 illustrates an example coupling mechanism that may couple the housing to the catheter adapter, according to some embodiments.

FIGS. 8A-8B illustrate the IV catheter system 68 in the retracted position, according to some embodiments. In some embodiments, when the IV catheter system 68 is in the retracted position, the IV catheter system 68 may be configured to allow removal of the housing 16, which may contain and shield the introducer needle 26, from the catheter adapter 12. In some embodiments, the catheter 14 may remain in the vasculature of the patient when the housing 16 is removed from the catheter adapter 12. In some embodiments, when the IV catheter system 68 is in the retracted position, the distal tip 26 and/or the distal end 32 of the guidewire 20 may be disposed proximal to a distal end of the housing 16. In some embodiments, the housing 16 may encapsulate the introducer needle 18 and/or the guidewire 20 when the IV catheter system 68 is in the retracted position.

In some embodiments, the IV catheter system 68 may include or correspond to one or more of the following: the IV catheter system 10 of FIGS. 1-3C, the IV catheter system 62 of FIG. 3D, and the IV catheter system 66 of FIG. 4. In further detail, in some embodiments, one or more of the IV catheter system 10, the IV catheter system 62, and the IV catheter system 66 may include one or more features of the catheter system 68. In some embodiments, the IV catheter system 68 may include one or more features of one or more of the following: the IV catheter system 10, the IV catheter system 62, and the IV catheter system 66.

Figure 10:
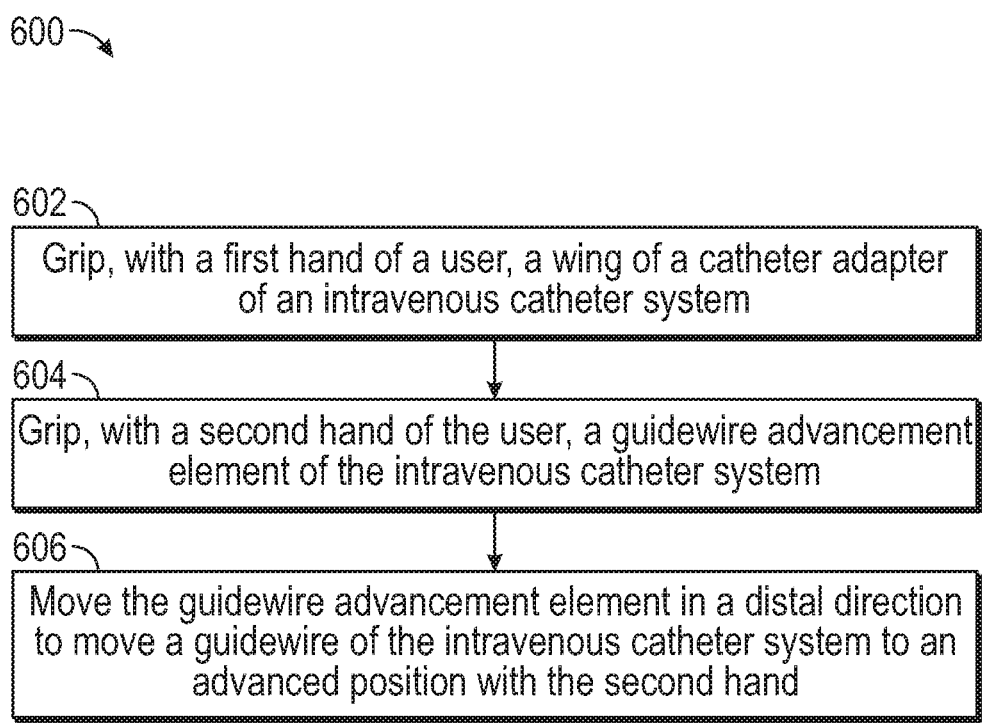
FIG. 10 is a block diagram illustrating an example method of IV catheter insertion into vasculature of a patient, according to some embodiments.

Referring now to FIG. 10, in some embodiments, a method 600 of IV catheter insertion into vasculature of a patient may begin at block 602. At block 602, a wing of the catheter adapter and/or a grip of the housing of an IV catheter system include may be gripped with a first hand of a user. In some embodiments, the IV catheter system may include or correspond to one or more of the following: the IV catheter system 10, the IV catheter system 62, the IV catheter system 66, and the IV catheter system 68.

Block 602 may be followed by block 604. At block 604, in some embodiments, a guidewire advancement element of the IV catheter system may be gripped with a second hand of the user. Block 604 may be followed by block 606. At block 606, the guidewire advancement element may be moved, with the second hand, in the distal direction to move a guidewire of the IV catheter system to the advanced position.

Although illustrated as discrete blocks, various blocks may be divided into additional blocks, combined into fewer blocks, or eliminated, depending on the desired implementation. Furthermore, the order of the blocks may be changed. Also, additional blocks may be added. For example, the method 600 may include inserting the introducer needle and the catheter into the vein when one or more of the following are being gripped: the wing of the catheter adapter, the grip of the housing, and the guidewire advancement element. In some embodiments, after the introducer needle and the catheter are inserted into the vein, the method may include moving the guidewire advancement element in the distal direction to move the guidewire to the advanced position with the second hand. In some embodiments, after the guidewire advancement element is moved in the distal direction to the advanced position, the catheter may be further advanced into the vein by moving the catheter adapter distally while holding the grip stationary.

In some embodiments, the first hand may correspond to the right hand of the user, and the second hand may correspond to the left hand of the user. In some embodiments, the gripping of the wing with the first hand of the user and the gripping of the guidewire advancement element with the second hand of the user may occur at a same time or simultaneously. In some embodiments, the guide wide advancement element may be moved in the distal direction when the guide wide advancement element is gripped. In some embodiments, the wing of a catheter adapter of the IV catheter system may be laterally offset from the guidewire advancement element, which may facilitate use of both hands of the user with respect to the IV catheter system. For example, the wing and the guidewire advancement element may be disposed on opposite sides of the IV catheter system.

In some embodiments, the IV catheter system may be configured to be gripped by the user according to a number grips that may facilitate insertion of the introducer needle into the vasculature of the patient and/or advancement of a catheter of the IV catheter system along the guidewire. For example, gripping the wing of the catheter adapter via a nested winged grip may include sandwiching the wing and the grip between a thumb and index finger of the first hand of the user. In some embodiments, the wing and the grip may be sandwiched between the thumb and the index finger of the first hand of the user at a same time as the guidewire advancement element is advanced distally and/or moved proximally with the second hand.

In some embodiments, the wing may be a first wing, and the catheter adapter may include a second wing opposite the first wing. Thus, in some embodiments, the catheter adapter may include multiple wings, such as, for example, the wing extending outwardly from the right side of the body of the catheter adapter and another wing extending outwardly from the left side of the body of the catheter adapter.

In some embodiments, gripping the first wing may include placing a middle finger of the first hand on an upper surface of the first wing. In some embodiments, at a same time as the first wing of the catheter adapter is gripped with the first hand and the guidewire advancement element is gripped with the second hand, the user may grip the second wing and the thumb tab by placing an index finger of the first hand on an upper surface of the second wing and a thumb of the first hand on the thumb tab, which may be referred to as the ported grip.

In some embodiments, the IV catheter system may not include the first wing. In these and other embodiments, the first hand of the user may grip the grip without gripping the first wing. In some embodiments, the grip may be gripped with the first hand at a same time as the guidewire advancement element is gripped with the second hand. In some embodiments, gripping the grip may include squeezing the grip between the index finger of the first hand of the user and the thumb of the first hand of the user. In some embodiments, the IV catheter system may not include the second wing.

In some embodiments, the method 600 may include moving the guidewire advancement element and/or the grip along the slot in the proximal direction. In some embodiments, in response to moving the guidewire advancement element and/or the grip along the slot in the proximal direction, the guidewire, the grip, and the introducer needle may move towards the proximal end of the housing.

In some embodiments, the method 600 may include moving the grip along the other slot in the proximal direction, and the guidewire, the guidewire advancement element, and the introducer needle may move towards the proximal end of the housing in response to moving the grip along the other slot.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. An intravenous catheter system, comprising:
    an integrated catheter adapter having a distal end, a proximal end, and a side port;
    a housing having a body extending along a longitudinal axis, a distal end, and a proximal end, wherein a central plane of the housing extends along the longitudinal axis to divide a left side of the body from a right side of the body, the housing further comprising a slot disposed on the left side and extending through the body from an interior of the body to an exterior of the body, wherein the distal end of the housing is coupled to a proximal end of the integrated catheter adapter and configured to directly couple to the proximal end of the integrated catheter adapter;
    an introducer needle having a proximal end, a distal tip, and a needle lumen extending between the proximal end of the introducer needle and the distal tip, wherein the proximal end of the introducer needle is secured within the housing;
    a guidewire disposed within the needle lumen; and
    a guidewire advancement element coupled to the guidewire and extending through the slot and moveable along the slot in a distal direction to move the guidewire from a retracted position to an advanced position, wherein the guidewire extends beyond the distal tip of the introducer needle when the guidewire is in the advanced position, wherein the guidewire advancement element is disposed on the left side of the housing.

2. The intravenous catheter system of claim 1, wherein the integrated catheter adapter further comprises a septum, wherein a fluid pathway of the intravenous catheter system does not extend through the septum, wherein the guidewire advancement element is moveable along the slot in the distal direction to advance the guidewire through the septum.

3. The intravenous catheter system of claim 1, wherein the integrated catheter adapter comprises a wing extending outwardly from the right side of the body of the integrated catheter adapter.

4. The intravenous catheter system of claim 1, wherein the housing further comprises a thumb tab.

5. The intravenous catheter system of claim 1, wherein the distal end of the housing is directly coupled to the proximal end of the integrated catheter adapter.

6. The intravenous catheter system of claim 1, wherein the body of the housing is cylindrical.

7. The intravenous catheter system of claim 1, wherein at least a portion of the guidewire advancement element extends laterally from the exterior of the left side of the body through the slot and is moveable along the slot in a distal direction to move the guidewire from a retracted position to an advanced position.

8. An intravenous catheter system, comprising:
- an integrated catheter adapter having a distal end, a proximal end, and a side port;
- a housing having a cylindrical body extending along a longitudinal axis, a distal end, and a proximal end, wherein a central plane extends along the longitudinal axis to divide a left side of the body from a right side of the body, the housing further comprising a slot disposed on the left side and extending from an interior of the body to an exterior of the body, wherein the distal end of the housing is configured to directly couple to the proximal end of the integrated catheter adapter;
- an introducer needle having a proximal end, a distal tip, and a needle lumen extending between the proximal end of the introducer needle and the distal tip, wherein the proximal end of the introducer needle is secured within the housing;
- a guidewire disposed within the needle lumen; and
- a guidewire advancement element coupled to the guidewire, wherein at least a portion of the guidewire advancement element extends laterally from the exterior of the left side of the body through the slot and is moveable along the slot in a distal direction to move the guidewire from a retracted position to an advanced position, wherein the guidewire extends beyond the distal tip of the introducer needle when the guidewire is in the advanced position.

* * * * *